US012702546B2

(12) United States Patent
Nir et al.

(10) Patent No.: US 12,702,546 B2
(45) Date of Patent: Aug. 11, 2026

(54) PROSTHETIC HEART VALVE LEAFLET ASSEMBLIES AND METHODS

(71) Applicant: Edwards Lifesciences Corporation, Irvine, CA (US)

(72) Inventors: Noam Nir, Pardes-Hanna (IL); Michael Bukin, Pardes Hanna (IL); Elena Sherman, Pardes Hana (IL)

(73) Assignee: Edwards Lifesciences Corporation, Irvine, CA (US)

( * ) Notice: Subject to any disclaimer, the term of this patent is extended or adjusted under 35 U.S.C. 154(b) by 1142 days.

(21) Appl. No.: 17/730,524

(22) Filed: Apr. 27, 2022

(65) Prior Publication Data

US 2022/0249227 A1 Aug. 11, 2022

Related U.S. Application Data

(63) Continuation of application No. PCT/US2020/057527, filed on Oct. 27, 2020.
(Continued)

(51) Int. Cl.
*A61F 2/24* (2006.01)

(52) U.S. Cl.
CPC .......... *A61F 2/2415* (2013.01); *A61F 2/2418* (2013.01); *A61F 2210/0076* (2013.01); *A61F 2220/0075* (2013.01)

(58) Field of Classification Search
None
See application file for complete search history.

(56) References Cited

U.S. PATENT DOCUMENTS

| | | | |
|---|---|---|---|
| 3,409,013 | A | 11/1968 | Berry |
| 3,548,417 | A | 12/1970 | Kisher |

(Continued)

FOREIGN PATENT DOCUMENTS

| | | | |
|---|---|---|---|
| DE | 0144167 | C | 9/1903 |
| DE | 2246526 | A1 | 3/1973 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp 704-708. 1992.

(Continued)

*Primary Examiner* — Megan Y Wolf
(74) *Attorney, Agent, or Firm* — Klarquist Sparkman, LLP

(57) ABSTRACT

A leaflet assembly for a prosthetic heart valve is disclosed. As one example, a method includes: forming a plurality of leaflet sub-assemblies, each including a leaflet and a skirt and formed by placing the skirt on one side of the leaflet such that the skirt extends along a curved cusp edge portion and two commissure tabs of the leaflet, folding two end portions of the skirt around corresponding commissures tabs, stitching each folded end portion to a corresponding commissure tab to form a respective half commissure portion, and stitching the skirt to the cusp edge portion and forming the leaflet assembly by pairing each half commissure portion of each leaflet sub-assembly with a half commissure portion of another leaflet sub-assembly to form a plurality of pairs of adjacent half commissure portions, and for each pair, stitching the adjacent half commissure portions to each other to form a commissure.

10 Claims, 9 Drawing Sheets

Related U.S. Application Data

(60) Provisional application No. 62/928,993, filed on Oct. 31, 2019.

(56) References Cited

U.S. PATENT DOCUMENTS 3,587,115 A 6/1971 Shiley
3,657,744 A 4/1972 Ersek
3,671,979 A 6/1972 Moulopoulos
3,714,671 A 2/1973 Edwards et al.
3,755,823 A 9/1973 Hancock
4,035,849 A 7/1977 Angell et al.
4,056,854 A 11/1977 Boretos et al.
4,106,129 A 8/1978 Carpentier et al.
4,222,126 A 9/1980 Boretos et al.
4,265,694 A 5/1981 Boretos et al.
4,297,749 A 11/1981 Davis et al.
4,339,831 A 7/1982 Johnson
4,343,048 A 8/1982 Ross et al.
4,345,340 A 8/1982 Rosen
4,373,216 A 2/1983 Klawitter
4,406,022 A 9/1983 Roy
4,441,216 A 4/1984 Ionescu et al.
4,470,157 A 9/1984 Love
4,535,483 A 8/1985 Klawitter et al.
4,574,803 A 3/1986 Storz
4,592,340 A 6/1986 Boyles
4,605,407 A 8/1986 Black et al.
4,612,011 A 9/1986 Kautzky
4,643,732 A 2/1987 Pietsch et al.
4,655,771 A 4/1987 Wallsten
4,692,164 A 9/1987 Dzemeshkevich et al.
4,733,665 A 3/1988 Palmaz
4,759,758 A 7/1988 Gabbay
4,762,128 A 8/1988 Rosenbluth
4,777,951 A 10/1988 Cribier et al.
4,787,899 A 11/1988 Lazarus
4,787,901 A 11/1988 Baykut
4,796,629 A 1/1989 Grayzel
4,820,299 A 4/1989 Philippe et al.
4,829,990 A 5/1989 Thuroff et al.
4,851,001 A 7/1989 Taheri
4,856,516 A 8/1989 Hillstead
4,878,495 A 11/1989 Grayzel
4,878,906 A 11/1989 Lindemann et al.
4,883,458 A 11/1989 Shiber
4,922,905 A 5/1990 Strecker
4,966,604 A 10/1990 Reiss
4,979,939 A 12/1990 Shiber
4,986,830 A 1/1991 Owens et al.
4,994,077 A 2/1991 Dobben
5,007,896 A 4/1991 Shiber
5,026,366 A 6/1991 Leckrone
5,032,128 A 7/1991 Alonso
5,037,434 A 8/1991 Lane
5,047,041 A 9/1991 Samuels
5,059,177 A 10/1991 Towne et al.
5,080,668 A 1/1992 Bolz et al.
5,085,635 A 2/1992 Cragg
5,089,015 A 2/1992 Ross
5,152,771 A 10/1992 Sabbaghian et al.
5,163,953 A 11/1992 Vince
5,167,628 A 12/1992 Boyles
5,192,297 A 3/1993 Hull
5,266,073 A 11/1993 Wall
5,282,847 A 2/1994 Trescony et al.
5,295,958 A 3/1994 Shturman
5,332,402 A 7/1994 Teitelbaum
5,360,444 A 11/1994 Kusuhara
5,370,685 A 12/1994 Stevens
5,397,351 A 3/1995 Pavcnik et al.
5,411,055 A 5/1995 Kane
5,411,552 A 5/1995 Andersen et al.
5,443,446 A 8/1995 Shturman
5,480,424 A 1/1996 Cox
5,500,014 A 3/1996 Quijano et al.
5,545,209 A 8/1996 Roberts et al.
5,545,214 A 8/1996 Stevens
5,549,665 A 8/1996 Vesely et al.
5,554,185 A 9/1996 Block et al.
5,558,644 A 9/1996 Boyd et al.
5,571,175 A 11/1996 Vanney et al.
5,584,803 A 12/1996 Stevens et al.
5,591,185 A 1/1997 Kilmer et al.
5,591,195 A 1/1997 Taheri et al.
5,607,464 A 3/1997 Trescony et al.
5,609,626 A 3/1997 Quijano et al.
5,628,792 A 5/1997 Lentell
5,639,274 A 6/1997 Fischell et al.
5,665,115 A 9/1997 Cragg
5,716,417 A 2/1998 Girard et al.
5,728,068 A 3/1998 Leone et al.
5,749,890 A 5/1998 Shaknovich
5,756,476 A 5/1998 Epstein et al.
5,769,812 A 6/1998 Stevens et al.
5,800,508 A 9/1998 Goicoechea et al.
5,840,081 A 11/1998 Andersen et al.
5,855,597 A 1/1999 Jayaraman
5,855,601 A 1/1999 Bessler et al.
5,855,602 A 1/1999 Angell
5,925,063 A 7/1999 Khosravi
5,957,949 A 9/1999 Leonhardt et al.
6,027,525 A 2/2000 Suh et al.
6,132,473 A 10/2000 Williams et al.
6,168,614 B1 1/2001 Andersen et al.
6,171,335 B1 1/2001 Wheatley et al.
6,174,327 B1 1/2001 Mertens et al.
6,210,408 B1 4/2001 Chandrasekaran et al.
6,217,585 B1 4/2001 Houser et al.
6,221,091 B1 4/2001 Khosravi
6,231,602 B1 5/2001 Carpentier et al.
6,245,102 B1 6/2001 Jayaraman
6,299,637 B1 10/2001 Shaolian et al.
6,302,906 B1 10/2001 Goecoechea et al.
6,350,277 B1 2/2002 Kocur
6,352,547 B1 3/2002 Brown et al.
6,425,916 B1 7/2002 Garrison et al.
6,440,764 B1 8/2002 Focht et al.
6,454,799 B1 9/2002 Schreck
6,458,153 B1 10/2002 Bailey et al.
6,461,382 B1 10/2002 Cao
6,468,660 B2 10/2002 Ogle et al.
6,482,228 B1 11/2002 Norred
6,488,704 B1 12/2002 Connelly et al.
6,527,979 B2 3/2003 Constantz
6,569,196 B1 5/2003 Vesely
6,582,462 B1 6/2003 Andersen et al.
6,605,112 B1 8/2003 Moll et al.
6,652,578 B2 11/2003 Bailey et al.
6,689,123 B2 2/2004 Pinchasik
6,716,244 B2 4/2004 Klaco
6,730,118 B2 5/2004 Spenser et al.
6,733,525 B2 5/2004 Yang et al.
6,767,362 B2 7/2004 Schreck
6,769,161 B2 8/2004 Brown et al.
6,783,542 B2 8/2004 Eidenschink
6,830,584 B1 12/2004 Seguin
6,878,162 B2 4/2005 Bales et al.
6,893,460 B2 5/2005 Spenser et al.
6,908,481 B2 6/2005 Cribier
6,936,067 B2 8/2005 Buchanan
7,018,406 B2 3/2006 Seguin et al.
7,018,408 B2 3/2006 Bailey et al.
7,096,554 B2 8/2006 Austin et al.
7,225,518 B2 6/2007 Eidenschink et al.
7,276,078 B2 10/2007 Spenser et al.
7,276,084 B2 10/2007 Yang et al.
7,318,278 B2 1/2008 Zhang et al.
7,374,571 B2 5/2008 Pease et al.
7,393,360 B2 7/2008 Spenser et al.
7,462,191 B2 12/2008 Spenser et al.
7,510,575 B2 3/2009 Spenser et al.
7,563,280 B2 7/2009 Anderson et al.
7,585,321 B2 9/2009 Cribier
7,618,446 B2 11/2009 Andersen et al.

(56) References Cited

U.S. PATENT DOCUMENTS

| | | | |
|---|---|---|---|
| 7,618,447 | B2 | 11/2009 | Case et al. |
| 7,655,034 | B2 | 2/2010 | Mitchell et al. |
| 7,785,366 | B2 | 8/2010 | Maurer et al. |
| 7,959,672 | B2 | 6/2011 | Salahieh et al. |
| 7,993,394 | B2 | 8/2011 | Hariton et al. |
| 8,029,556 | B2 | 10/2011 | Rowe |
| 8,167,932 | B2 | 5/2012 | Bourang |
| 8,291,570 | B2 | 10/2012 | Eidenschink et al. |
| 8,449,606 | B2 | 5/2013 | Eliasen et al. |
| 8,454,685 | B2 | 6/2013 | Hariton et al. |
| 8,652,203 | B2 | 2/2014 | Quadri et al. |
| 8,747,463 | B2 | 6/2014 | Fogarty et al. |
| 9,078,781 | B2 | 7/2015 | Ryan et al. |
| 11,224,509 | B2 | 1/2022 | Dasi et al. |
| 2001/0021872 | A1 | 9/2001 | Bailey et al. |
| 2002/0026094 | A1 | 2/2002 | Roth |
| 2002/0032481 | A1 | 3/2002 | Gabbay |
| 2002/0138135 | A1 | 9/2002 | Duerig et al. |
| 2002/0173842 | A1 | 11/2002 | Buchanan |
| 2003/0050694 | A1 | 3/2003 | Yang et al. |
| 2003/0100939 | A1 | 5/2003 | Yodfat et al. |
| 2003/0158597 | A1 | 8/2003 | Quiachon et al. |
| 2003/0212454 | A1 | 11/2003 | Scott et al. |
| 2004/0039436 | A1 | 2/2004 | Spenser et al. |
| 2004/0186563 | A1 | 9/2004 | Lobbi |
| 2004/0186565 | A1 | 9/2004 | Schreck |
| 2004/0260389 | A1 | 12/2004 | Case et al. |
| 2005/0010285 | A1 | 1/2005 | Lambrecht et al. |
| 2005/0075725 | A1 | 4/2005 | Rowe |
| 2005/0075728 | A1 | 4/2005 | Nguyen et al. |
| 2005/0096736 | A1 | 5/2005 | Osse et al. |
| 2005/0188525 | A1 | 9/2005 | Weber et al. |
| 2005/0203614 | A1 | 9/2005 | Forster et al. |
| 2005/0203617 | A1 | 9/2005 | Forster et al. |
| 2005/0234546 | A1 | 10/2005 | Nugent et al. |
| 2006/0004469 | A1 | 1/2006 | Sokel |
| 2006/0025857 | A1 | 2/2006 | Bergheim et al. |
| 2006/0058872 | A1 | 3/2006 | Salahieh et al. |
| 2006/0074484 | A1 | 4/2006 | Huber |
| 2006/0149350 | A1 | 7/2006 | Patel et al. |
| 2006/0183383 | A1 | 8/2006 | Asmus et al. |
| 2006/0229719 | A1 | 10/2006 | Marquez et al. |
| 2006/0259137 | A1 | 11/2006 | Artof et al. |
| 2006/0287717 | A1 | 12/2006 | Rowe et al. |
| 2007/0005131 | A1 | 1/2007 | Taylor |
| 2007/0010876 | A1 | 1/2007 | Salahieh et al. |
| 2007/0010877 | A1 | 1/2007 | Salahieh et al. |
| 2007/0112422 | A1 | 5/2007 | Dehdashtian |
| 2007/0162102 | A1 | 7/2007 | Ryan et al. |
| 2007/0203503 | A1 | 8/2007 | Salahieh et al. |
| 2007/0203575 | A1 | 8/2007 | Forster et al. |
| 2007/0203576 | A1 | 8/2007 | Lee et al. |
| 2007/0213813 | A1 | 9/2007 | Von Segesser et al. |
| 2007/0233228 | A1 | 10/2007 | Eberhardt et al. |
| 2007/0260305 | A1 | 11/2007 | Drews et al. |
| 2007/0265700 | A1 | 11/2007 | Eliasen et al. |
| 2008/0114442 | A1 | 5/2008 | Mitchell et al. |
| 2008/0125853 | A1 | 5/2008 | Bailey et al. |
| 2008/0154355 | A1 | 6/2008 | Benichou et al. |
| 2008/0183271 | A1 | 7/2008 | Frawley et al. |
| 2008/0243245 | A1 | 10/2008 | Thambar et al. |
| 2008/0275537 | A1 | 11/2008 | Limon |
| 2009/0125118 | A1 | 5/2009 | Gong |
| 2009/0157175 | A1 | 6/2009 | Benichou |
| 2009/0276040 | A1 | 11/2009 | Rowe et al. |
| 2009/0281619 | A1 | 11/2009 | Le et al. |
| 2009/0299452 | A1 | 12/2009 | Eidenschink et al. |
| 2009/0319037 | A1 | 12/2009 | Rowe et al. |
| 2010/0049313 | A1 | 2/2010 | Alon et al. |
| 2010/0168844 | A1 | 7/2010 | Toomes et al. |
| 2010/0198347 | A1 | 8/2010 | Zakay et al. |
| 2010/0204781 | A1 | 8/2010 | Alkhatib |
| 2011/0015729 | A1 | 1/2011 | Jimenez et al. |
| 2011/0066224 | A1 | 3/2011 | White |
| 2011/0137397 | A1 | 6/2011 | Chau et al. |
| 2011/0218619 | A1 | 9/2011 | Benichou et al. |
| 2011/0319991 | A1 | 12/2011 | Hariton et al. |
| 2012/0089223 | A1 | 4/2012 | Nguyen et al. |
| 2012/0101571 | A1 | 4/2012 | Thambar et al. |
| 2012/0123529 | A1 | 5/2012 | Levi et al. |
| 2012/0172981 | A1* | 7/2012 | DuMontelle .......... A61F 2/2412 623/2.17 |
| 2012/0259409 | A1 | 10/2012 | Nguyen et al. |
| 2013/0023985 | A1 | 1/2013 | Khairkhahan et al. |
| 2013/0046373 | A1 | 2/2013 | Cartledge et al. |
| 2013/0150956 | A1 | 6/2013 | Yohanan et al. |
| 2013/0166017 | A1 | 6/2013 | Cartledge et al. |
| 2013/0190857 | A1 | 7/2013 | Mitra et al. |
| 2013/0274873 | A1 | 10/2013 | Delaloye et al. |
| 2013/0310926 | A1 | 11/2013 | Hariton |
| 2013/0317598 | A1 | 11/2013 | Rowe et al. |
| 2013/0331929 | A1 | 12/2013 | Mitra et al. |
| 2014/0194981 | A1 | 7/2014 | Menk et al. |
| 2014/0200661 | A1 | 7/2014 | Pintor et al. |
| 2014/0209238 | A1 | 7/2014 | Bonyuet et al. |
| 2014/0222136 | A1 | 8/2014 | Geist et al. |
| 2014/0277417 | A1 | 9/2014 | Schraut et al. |
| 2014/0277419 | A1 | 9/2014 | Garde et al. |
| 2014/0277424 | A1 | 9/2014 | Oslund |
| 2014/0277563 | A1 | 9/2014 | White |
| 2014/0330372 | A1 | 11/2014 | Weston et al. |
| 2014/0343671 | A1 | 11/2014 | Yohanan et al. |
| 2014/0350667 | A1 | 11/2014 | Braido et al. |
| 2015/0073545 | A1 | 3/2015 | Braido |
| 2015/0073546 | A1 | 3/2015 | Braido |
| 2017/0296337 | A1* | 10/2017 | Alkhatib ............... A61F 2/2436 |
| 2018/0028310 | A1* | 2/2018 | Gurovich ............. A61F 2/2433 |

FOREIGN PATENT DOCUMENTS

| | | | |
|---|---|---|---|
| DE | 19532846 | A1 | 3/1997 |
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| EP | 0103546 | A1 | 3/1984 |
| EP | 0850607 | A1 | 7/1998 |
| EP | 1057460 | A1 | 12/2000 |
| EP | 1088529 | A2 | 4/2001 |
| EP | 1570809 | A1 | 9/2005 |
| FR | 2788217 | A1 | 7/2000 |
| FR | 2815844 | A1 | 5/2002 |
| GB | 2056023 | A | 3/1981 |
| SU | 1271508 | A1 | 11/1986 |
| WO | 9117720 | A1 | 11/1991 |
| WO | 9217118 | A1 | 10/1992 |
| WO | 9301768 | A1 | 2/1993 |
| WO | 9724080 | A1 | 7/1997 |
| WO | 9829057 | A1 | 7/1998 |
| WO | 9930646 | A1 | 6/1999 |
| WO | 9933414 | A1 | 7/1999 |
| WO | 9940964 | A1 | 8/1999 |
| WO | 9947075 | A1 | 9/1999 |
| WO | 0018333 | A1 | 4/2000 |
| WO | 0041652 | A1 | 7/2000 |
| WO | 0047139 | A1 | 8/2000 |
| WO | 0135878 | A2 | 5/2001 |
| WO | 0149213 | A2 | 7/2001 |
| WO | 0154624 | A1 | 8/2001 |
| WO | 0154625 | A1 | 8/2001 |
| WO | 0162189 | A1 | 8/2001 |
| WO | 0164137 | A1 | 9/2001 |
| WO | 0176510 | A2 | 10/2001 |
| WO | 0222054 | A1 | 3/2002 |
| WO | 0236048 | A1 | 5/2002 |
| WO | 0241789 | A2 | 5/2002 |
| WO | 0243620 | A1 | 6/2002 |
| WO | 0247575 | A2 | 6/2002 |
| WO | 0249540 | A2 | 6/2002 |
| WO | 03047468 | A1 | 6/2003 |
| WO | 2005034812 | A1 | 4/2005 |

(56) References Cited

FOREIGN PATENT DOCUMENTS

| | | | |
|---|---|---|---|
| WO | 2005055883 | A1 | 6/2005 |
| WO | 2005084595 | A1 | 9/2005 |
| WO | 2005102015 | A2 | 11/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |

OTHER PUBLICATIONS

H.R. Andersen "History of Percutaneous Aortic Valve Prosthesis," Herz No. 34. pp 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

* cited by examiner

FIG. 2A 102
136
132
132
104
Z-axis
X-axis
130
134

FIG. 2B 122
102
122
104
126
Z-axis
124
X-axis
120

194
110'
104
122'
162'
164'
142'c
142'd
114'
X-axis
Y-axis
132'
142'e
142'f
166
142''f
142''e
132''
162''
122'
164''
142''c
142''d
114''
110''

194
110'
104
122'
162'
164'
142'c
142'd
114'
X-axis
Y-axis
132'
142'e
142'f
166
142''f
142''e
132''
162''
122'
164''
142''c
142''d
114''
110''

200
206
222
220
218
214
202
212
210
208

200
206
220
222
214
212
202
210
202
208
218

200
212
206
216
214
210
208
202
204
230
218
230

200
206
205
207
216
214
210
204
202
224
226
230
218
208
230

PROSTHETIC HEART VALVE LEAFLET ASSEMBLIES AND METHODS

CROSS REFERENCE TO RELATED APPLICATIONS

This application is a continuation of PCT Patent Application No. PCT/US2020/057527, filed Oct. 27, 2020, which claims the benefit of U.S. Provisional Application Ser. No. 62/928,993, filed Oct. 31, 2019, all of which applications are incorporated herein by reference.

FIELD

The present disclosure relates to prosthetic heart valves, and to methods and assemblies for forming leaflet assemblies and attaching leaflet assemblies to a frame of such prosthetic heart valves.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size.

Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve.

Most expandable, transcatheter heart valves comprise a cylindrical metal frame or stent and prosthetic leaflets mounted inside the frame. Typically, the leaflets are secured to a circumferential skirt, attached to an inner surface of the frame of the prosthetic valve. Such a traditional skirt can serve as an attachment surface for the valve leaflets, while also establishing a seal with the native tissue when the prosthetic valve is placed at the implantation site. However, since the skirt can span an entire circumference of the inner surface of the frame, attachment of multiple leaflets (e.g., three leaflets) to the skirt may be time consuming and require delicate assembly skills to ensure proper attachment.

Accordingly, a need exists for improved prosthetic heart valve leaflet assemblies and methods for assembling the leaflet assemblies to a frame of the prosthetic heart valve.

SUMMARY

Described herein are embodiments of methods for assembling a prosthetic heart valve including a leaflet assembly, methods of assembling a leaflet sub-assembly of the leaflet assembly, and prosthetic heart valves including a leaflet assembly. In some embodiments, a leaflet assembly for a prosthetic heart valve may be comprised of a plurality of leaflet sub-assemblies that are individually assembled and then connected together at adjacent half commissure portions to form commissures adapted to be coupled to commissure support portions of a frame of the prosthetic heart valve. In some embodiments, each leaflet sub-assembly may include a skirt and leaflet and be formed by placing the skirt on one side of the leaflet such that the skirt extends along a curved cusp edge portion of the leaflet and two commissure tabs of the leaflet, folding two end portions of the skirt around corresponding commissures tabs of the leaflet, stitching each folded end portion to a corresponding commissure tab of the two commissure tabs to form a respective half commissure portion of the leaflet sub-assembly, and stitching the skirt to the cusp edge portion of the leaflet.

In one representative embodiment, a method of assembling a prosthetic heart valve including a leaflet assembly can include: forming a plurality of leaflet sub-assemblies, each leaflet sub-assembly including a leaflet and a skirt, wherein each leaflet sub-assembly is formed by placing the skirt on one side of the leaflet such that the skirt extends along a curved cusp edge portion of the leaflet and two commissure tabs of the leaflet, folding two end portions of the skirt around corresponding commissures tabs of the leaflet, stitching each folded end portion to a corresponding commissure tab of the two commissure tabs to form a respective half commissure portion of the leaflet sub-assembly, and stitching the skirt to the cusp edge portion of the leaflet; forming the leaflet assembly by pairing each half commissure portion of each leaflet sub-assembly with a half commissure portion of another leaflet sub-assembly of the plurality of leaflet sub-assemblies to form a plurality of pairs of adjacent half commissure portions, and for each pair, stitching the adjacent half commissure portions to each other to form a commissure of the leaflet assembly; and securing the leaflet assembly to a frame of the prosthetic heart valve via fastening each commissure to a commissure support portion of the frame.

In some embodiments, the method can further include securing the leaflet assembly to the frame of the prosthetic heart valve via fastening the skirt of each leaflet sub-assembly to struts of the frame.

In some embodiments, fastening the skirt of each leaflet sub-assembly to struts of the frame includes fastening a skirt middle portion of the skirt of each leaflet sub-assembly to a plurality of interconnected struts of the frame that are arranged in a lattice-type pattern, where the skirt middle portion is arranged between two tabs of the skirt.

In some embodiments, each of the two end portions of the skirt includes a tab and folding the two end portions of the skirt around corresponding commissure tabs of the leaflet includes, for each end portion and corresponding commissure tab, folding the tab around the corresponding commissure tab to form a first flap covering a first side of the commissure tab and a second flap covering a second side of the commissure tab.

In some embodiments, each leaflet sub-assembly further includes a reinforcing strip and the method may further include placing the reinforcing strip on a side of the skirt arranged opposite the side of the skirt placed on the leaflet such that the reinforcing strip extends along a curved portion of the skirt and each of two end portions of the reinforcing strip overlay a corresponding first flap of the skirt and stitching each folded end portion of the skirt to the corresponding commissure tab and a corresponding end portion of the two end portions of the reinforcing strip via a first stitch.

In some embodiments, folding the two end portions of the skirt around corresponding tabs of the leaflet assembly further includes, for each end portion of the skirt and corresponding commissure tab, folding a free end portion of the first flap back over itself to cover the corresponding end portion of the reinforcing strip and form two overlapping layers over the first side of the commissure tab and folding a free end portion of the second flap back over itself to form two overlapping layers over the second side of the commissure tab.

In some embodiments, the method can further include stitching the two overlapping layers over the first side of the commissure tab, the commissure tab, and the two overlapping layers over the second side of the commissure tab to one another via a second stitch.

In some embodiments, for each pair of adjacent half commissure portions, stitching the adjacent half commissure portions to each other to form a commissure of the leaflet assembly includes stitching the adjacent half commissure portions to each other via a third stitch arranged adjacent to the first stitch, the third stitch extending through the corresponding end portion of the reinforcing strip of each leaflet sub-assembly.

In some embodiments, stitching the adjacent half commissure portions to each other via the third stitch includes extending the third stitch through the two overlapping layers over the first side of the commissure tab, the commissure tab, and the two overlapping layers over the second side of the commissure tab, for each half commissure portion of the pair of adjacent half commissure portions. In some embodiments, the third stitch is arranged adjacent to the first stitch on a side of the first stitch that faces the second stitch.

In some embodiments, stitching the adjacent half commissure portions to each other via the third stitch includes extending the third stitch through the two overlapping layers over the first side of the commissure tab and the commissure tab, and not the two overlapping layers over the second side of the commissure tab, for each half commissure portion of the pair of adjacent half commissure portions. In some embodiments, the third stitch is arranged adjacent to the first stitch on a side of the first stitch that is arranged opposite to a side of the first stitch that faces the second stitch.

In some embodiments, stitching the skirt to the cusp edge portion of the leaflet includes stitching the skirt to the cusp edge portion via a series of in-and-out stitches extending through the leaflet and the skirt, along the cusp edge portion from a first of the two commissure tabs of the leaflet to a second of the two commissure tabs of the leaflet.

In some embodiments, stitching the skirt to the cusp edge portion of the leaflet via the series of in-and-out stitches includes extending the series of in-and-out stitches through and along a first stitching line arranged on a skirt middle portion of the skirt that extends between the two end portions of the skirt.

In some embodiments, the first stitching line includes one or more external markings or apertures.

In some embodiments, each leaflet sub-assembly further includes a reinforcing strip. The method further comprises placing the reinforcing strip on a side of the skirt arranged opposite the side of the skirt placed on the leaflet such that the reinforcing strip extends along a curved portion of the skirt and each of two end portions of the reinforcing strip overlay a corresponding first flap of the skirt and stitching the reinforcing strip to the skirt via extending the series of in-and-out stitches through and along a second stitching line arranged along a curved, middle portion of the reinforcing strip. The first stitching line and the second stitching line are aligned with one another.

In some embodiments, for each pair of adjacent half commissure portions, stitching the adjacent half commissure portions to each other to form a commissure of the leaflet assembly includes stitching the adjacent half commissure portions to each together at bases of the two commissure portions, wherein a base of each commissure portion is arranged opposite a corresponding outer edge of the commissure portion, proximate to a cusp of a corresponding leaflet.

In some embodiments, fastening each commissure to a commissure support portion of the frame includes wrapping end portions of each commissure around a respective commissure support portion and stitching through the end portions of the commissure via one or more sutures and tying the one or more sutures together on an outer surface of the commissure support portion of the frame.

In another representative embodiment, a prosthetic heart valve can include: an annular frame comprising a plurality of commissure support portions and a leaflet assembly supported by the frame. The leaflet assembly can include a plurality of leaflet sub-assemblies, each leaflet sub-assembly including: a leaflet including a cusp edge portion and two leaflet tabs, each leaflet tab of the two leaflet tabs arranged at an opposing end of the cusp edge portion; a skirt including a skirt middle portion and two tabs, each tab of the two tabs arranged at an opposing end of the skirt middle portion, wherein each tab of the skirt is wrapped around and secured to a corresponding leaflet tab to form a half commissure portion at either end of the leaflet sub-assembly. Additionally, each half commissure portion is secured to an adjacent half commissure portion of an adjacent leaflet sub-assembly of the plurality of leaflet sub-assemblies to form a commissure of the leaflet assembly and each commissure is coupled to a corresponding commissure support portion of the frame.

In some embodiments, each half commissure portion is secured to an adjacent half commissure portion of an adjacent leaflet sub-assembly via a suture extending along and through bases of the adjacent half commissure portions, the bases arranged adjacent to corresponding cusps of leaflets of the leaflet sub-assemblies.

In some embodiments, the formed commissure includes two outer, free ends, arranged opposite an end of the commissure including ends of the adjacent half commissure portions that are secured to one another, that are wrapped around and coupled to the corresponding commissure support portion of the frame.

In some embodiments, each commissure is coupled to the corresponding commissure support portion of the frame by a series of stitches that extend across an outer surface of the commissure support portion.

In some embodiments, each skirt of each leaflet sub-assembly is coupled to struts of the frame.

In some embodiments, the skirt middle portion of the skirt of each leaflet sub-assembly includes one or more positioning guides arranged along an upper portion of the skirt middle portion that are configured to position the skirt middle portion relative to the struts of the frame.

In some embodiments, the one or more positioning guides are markings on the skirt or apertures formed in the skirt.

In some embodiments, for each leaflet sub-assembly, the skirt middle portion of the skirt is secured to the cusp edge portion of the leaflet via a series of in-and-out stitches.

In some embodiments, for each leaflet sub-assembly, each tab of the two tabs of the skirt includes one or more positioning guides that are configured to position the tab of the skirt relative to a corresponding leaflet tab of the two leaflet tabs of the leaflet.

In some embodiments, each half commissure portion is formed by multiple, overlapping layers of the tab of the skirt, on either side of the leaflet tab, secured to one another and through the leaflet tab via one or more fasteners.

In some embodiments, each half commissure portion is formed by two overlapping layers of the tab of the skirt on a first side of the leaflet tab, the leaflet tab, and two overlapping layers of the tab of the skirt on an opposite, second side of the leaflet tab and wherein a fastener extends through each of the two overlapping layers of the tab on the first side of the leaflet tab, the leaflet tab, and the two overlapping layers of the tab on the second side of the leaflet tab.

In some embodiments, each leaflet sub-assembly further comprises a reinforcing strip including a middle portion and two end portions, each end portion of the two end portions arranged at an opposing end of the middle portion, wherein each tab of the skirt is wrapped around and secured to the corresponding leaflet tab and a corresponding end portion of the reinforcing strip to form the half commissure portion at either end of the leaflet sub-assembly.

In some embodiments, each tab of the skirt is secured to the corresponding leaflet tab and the corresponding end portion of the reinforcing strip via a first fastener that extends through the corresponding end portion of the reinforcing strip, the corresponding leaflet tab, and flaps of the tab of the skirt arranged on either side of the corresponding leaflet tab.

In some embodiments, each tab of the skirt is further secured to the corresponding leaflet tab and the corresponding end portion of the reinforcing strip via a second fastener that extends through two overlapping layers of the tab of the skirt that are arranged on a first side of the corresponding leaflet tab, the leaflet tab, and two overlapping layers of the tab of the skirt that are arranged on an opposite, second side of the corresponding leaflet tab.

In some embodiments, the second fastener is arranged closer to an outer edge of the corresponding leaflet tab than the first fastener.

In some embodiments, the commissure support portion of the frame includes an actuator of the frame that is configured to apply expansion and compression forces to the frame for radially expanding and compressing the prosthetic valve.

In some embodiments, the commissure support portion of the frame includes a support strut or post of the frame.

In some embodiments, the leaflet assembly comprises three leaflet sub-assemblies.

In yet another representative embodiment, a method of assembling a leaflet sub-assembly of a prosthetic valve can include: arranging a skirt of the leaflet sub-assembly over a leaflet of the sub-assembly so that a curved, middle portion of the skirt is aligned with a curved, cusp edge portion of the leaflet and each tab of two tabs of the skirt overlaps a corresponding one leaflet tab of two leaflet tabs of the leaflet; at each end of the leaflet sub-assembly, wrapping the tab of the skirt around the corresponding leaflet tab of the leaflet to form a first flap covering a first side of the leaflet tab and a second flap covering a second side of the leaflet tab; arranging a reinforcing strip over the skirt so that a contour of a middle portion of the reinforcing strip is aligned with a contour of the cusp edge portion of the leaflet and the middle portion of the skirt and each end portion of two end portions of the reinforcing strip overlaps a corresponding first flap; and at each end of the leaflet sub-assembly: securing the end portion of the reinforcing strip to the corresponding leaflet tab of the leaflet and tab of the skirt; folding a free end portion of the first flap back over itself to cover the end portion of the reinforcing strip and form two overlapping layers over the first side of the leaflet tab and folding a free end portion of the second flap back over itself to form two overlapping layers over the second side of the leaflet tab; and securing the two overlapping layers over the first side of the leaflet tab, the leaflet tab, and the two overlapping layers over the second side of the leaflet tab to one another.

In some embodiments, the method can further include securing the middle portion of the skirt, the cusp edge portion of the leaflet, and the middle portion of the reinforcing strip to one another.

In some embodiments, securing the end portion of the reinforcing strip to the corresponding leaflet tab of the leaflet and tab of the skirt includes extending a first stitch through each of the end portion of the reinforcing strip, the first flap, the leaflet tab, and the second flap.

In some embodiments, securing the two overlapping layers over the first side of the leaflet tab, the leaflet tab, and the two overlapping layers over the second side of the leaflet tab to one another includes extending a second stitch through each of the two overlapping layers over the first side of the leaflet tab, the leaflet tab, and the two overlapping layers over the second side of the leaflet tab, adjacent to the first stitch and outside the first stitch relative to an outer edge of the leaflet tab.

In another representative embodiment, a leaflet sub-assembly for a leaflet assembly of a prosthetic heart valve can comprise: a leaflet including a cusp edge portion and two leaflet tabs, each leaflet tab of the two leaflet tabs arranged at an opposing end of the cusp edge portion; a skirt including a skirt middle portion and two tabs, each tab of the two tabs arranged at an opposing end of the skirt middle portion, the skirt arranged against the leaflet so that the middle portion of the skirt is aligned with the cusp edge portion of the leaflet and each tab of the two tabs of the skirt overlaps a corresponding leaflet tab of the two leaflet tabs of the leaflet, wherein each tab of the skirt is wrapped around the corresponding leaflet tab of the leaflet to form a first flap covering a first side of the corresponding leaflet tab and a second flap covering a second side of the corresponding leaflet tab; and a reinforcing strip including a middle portion and two end portions, each end portion of the two end portions arranged at an opposing end of the middle portion, the reinforcing strip arranged against the skirt such that a contour of the middle portion of the reinforcing strip is aligned with a contour of the cusp edge portion of the leaflet and the middle portion of the skirt and each end portion of two end portions of the reinforcing strip overlaps a corresponding first flap. For each leaflet tab, a free end portion of the corresponding first flap is folded back over itself to cover the corresponding end portion of the reinforcing strip and form two overlapping layers over the first side of the corresponding leaflet tab and a free end portion of the corresponding second flap is folded back over itself to form two overlapping layers over the second side of the corresponding leaflet tab.

In some embodiments, for each leaflet tab, each of the corresponding end portion of the reinforcing strip, the first flap, the leaflet tab, and the second flap are secured together via a first fastener.

In some embodiments, for each leaflet tab, each of the corresponding leaflet tab, the two overlapping layers over the first side of the leaflet tab, and the two overlapping layers over the second side of the leaflet tab are secured together via a second fastener.

In some embodiments, the second fastener is arranged adjacent to the first fastener and closer to an outer edge of the corresponding leaflet tab than the first fastener.

In some embodiments, the middle portion of the reinforcing strip, the skirt middle portion of the skirt, and the cusp edge portion of the leaflet are secured together via an additional fastener.

In some embodiments, the additional fastener is a plurality of in-and-out stitches.

In some embodiments, the middle portion of the reinforcing strip includes a first stitching line arranged along its center, following a curved shape of the middle portion and the skirt middle portion includes a second stitching line centered along a length of the skirt middle portion, the first stitching line and the second stitching line overlapping one another.

In some embodiments, the skirt includes one or more positioning guides arranged along an upper portion of the skirt middle portion configured as marking or apertures formed in the skirt.

In some embodiments, each tab of the two tabs of the skirt includes one or more columns of positioning guides that are configured as marking or apertures formed in the skirt.

In some embodiments, each tab of the two tabs of the skirt extends outward from one end of the skirt middle portion, in a direction parallel to a centerline of the skirt, and in a direction perpendicular to and away from the centerline.

The foregoing and other objects, features, and advantages of the invention will become more apparent from the following detailed description, which proceeds with reference to the accompanying figures.

BRIEF DESCRIPTION OF THE DRAWINGS

FIGS. 2A-2C are plan views of individual components of a leaflet sub-assembly, including a leaflet, reinforcing strip, and a skirt, for a prosthetic heart valve.

DETAILED DESCRIPTION

Described herein are examples of prosthetic heart valves, leaflet assemblies for prosthetic heart valves, leaflet sub-assemblies of a leaflet assembly, and methods for assembling leaflet sub-assemblies, leaflet assemblies including a plurality of leaflet sub-assemblies, and prosthetic heart valves including the leaflet assemblies. The prosthetic heart valves may include a frame and a leaflet assembly attached to the frame. The leaflet assembly may include a plurality of leaflet sub-assemblies coupled to one another at adjacent half commissure portions of the leaflet sub-assemblies. Each leaflet sub-assembly can include a leaflet (e.g., valve leaflet) and a skirt coupled to one another along a cusp edge portion of the leaflet and at a half commissure portion formed at either end of the cusp edge portion. Each half commissure portion can be formed by folding a tab of the skirt around a corresponding leaflet (e.g., commissure) tab of the leaflet and securing them to one another. Half commissure portions of adjacently arranged leaflet sub-assemblies can then be coupled to one another, prior to being attached to the frame of the prosthetic heart valve. As a result, a leaflet assembly for a prosthetic heart valve may be more easily assembled off the frame of the prosthetic heart valve and a time and effort for securing the leaflet assembly to the frame of the prosthetic heart valve may be reduced.

Figure 1:
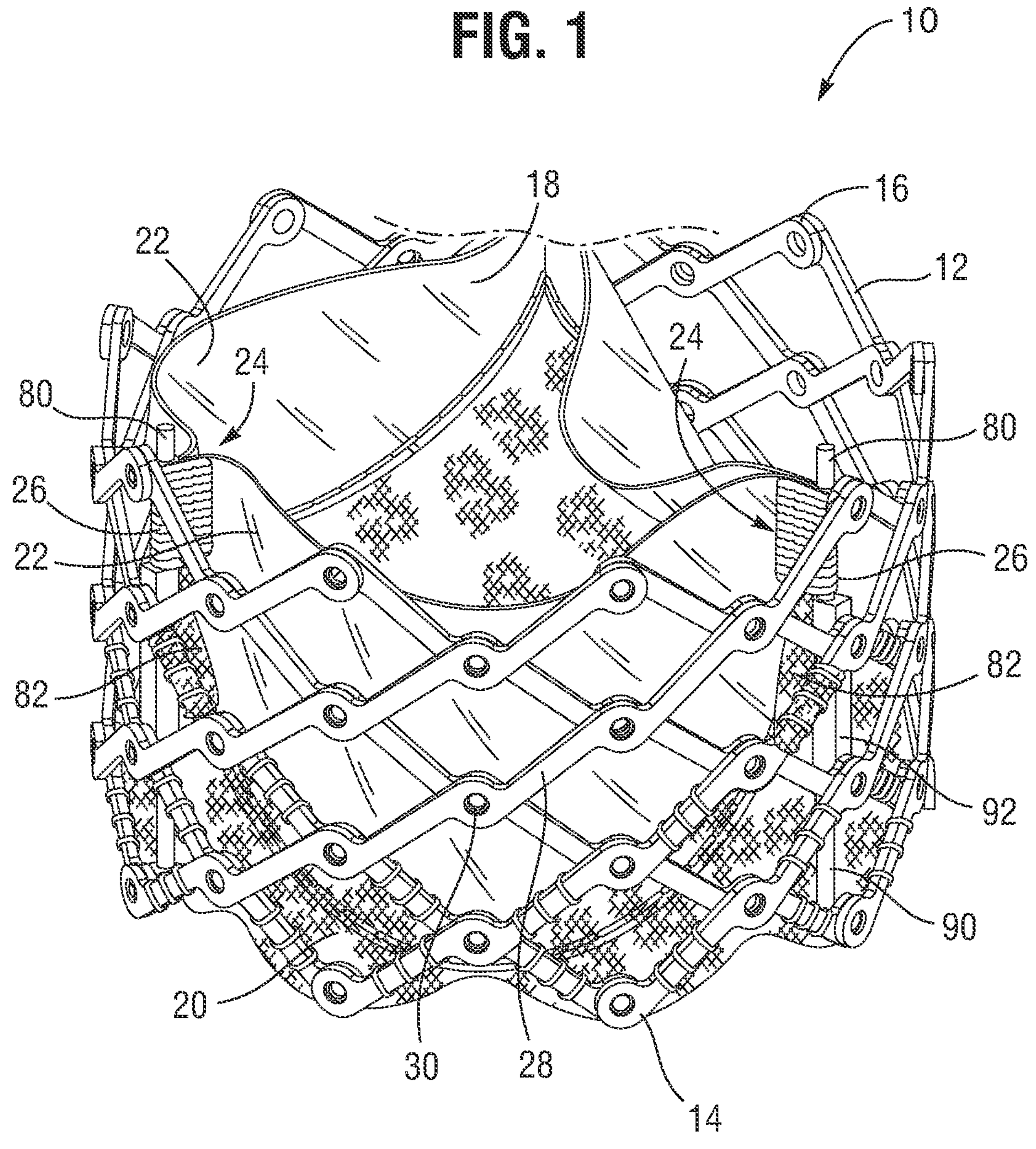
FIG. 1 is a perspective view of an exemplary embodiment of a prosthetic heart valve.

FIG. 1 shows an exemplary prosthetic heart valve 10, according to one embodiment. The prosthetic heart valve 10 can be radially compressible and expandable between a radially compressed configuration for delivery into a patient and a radially expanded configuration. In particular embodiments, the prosthetic heart valve 10 can be implanted within the native aortic annulus, although it also can be implanted at other locations in the heart, including within the native mitral valve, the native pulmonary valve, and the native tricuspid valve. The prosthetic heart valve 10 can include an annular stent or frame 12 having a first end 14 and a second end 16.

In the depicted embodiment, the first end 14 is an inflow end and the second end 16 is an outflow end. The outflow end 16 can be coupled to a delivery apparatus for delivering and implanting the prosthetic heart valve within the native aortic valve is a transfemoral, retrograde delivery approach. Thus, in the delivery configuration of the prosthetic heart valve, the outflow end 16 is the proximal-most end of the prosthetic valve. In other embodiments, the inflow end 14 can be coupled to the delivery apparatus, depending on the particular native valve being replaced and the delivery technique that is used (e.g., trans-septal, transapical, etc.). For example, the inflow end 14 can be coupled to the delivery apparatus (and therefore is the proximal-most end of the prosthetic heart valve in the delivery configuration)

when delivering the prosthetic heart valve to the native mitral valve via a trans-septal delivery approach.

The frame 12 can be made of any of various suitable materials, such as stainless steel, a cobalt chromium alloy, or a nickel titanium alloy ("NiTi"), for example Nitinol. Referring again to FIG. 1, as shown, the frame 12 can include a plurality of interconnected struts 28 arranged in a lattice-type pattern. The struts 28 are shown as positioned diagonally, or offset at an angle relative to, and radially offset from, a longitudinal axis of the prosthetic heart valve 10 when the prosthetic heart valve 10 is in the expanded configuration. In other implementations, the struts 28 can be offset by a different amount than depicted in FIG. 1, or some or all of the struts 28 can be positioned parallel to the longitudinal axis of the prosthetic heart valve 10.

In the illustrated embodiment, the struts 28 are pivotably coupled to one another at one or more pivot joints along the length of each strut. For example, in the illustrated configuration, each of the struts 28 can be formed with apertures at opposing ends of the strut and apertures spaced along the length of the strut. Respective hinges can be formed at the locations where struts 28 overlap each other via fasteners or pivot members, such as rivets or pins 30 that extend through the apertures. The hinges can allow the struts 28 to pivot relative to one another as the frame 12 is radially expanded or compressed, such as during assembly, preparation, or implantation of the prosthetic heart valve 10.

In some embodiments, the frame 12 can be constructed by forming individual components (e.g., the struts and fasteners of the frame) and then mechanically assembling and connecting the individual components together. In other embodiments, the struts 28 are not coupled to each other with respective hinges but are otherwise pivotable or bendable relative to each other to permit radial expansion and contraction of the frame 12. For example, the frame 12 can be formed (e.g., via laser cutting, electroforming or physical vapor deposition) from a single piece of material (e.g., a metal tube). Further details regarding the construction of the frame and the prosthetic heart valve are described in U.S. Patent Application Publication Nos. 2018/0153689, 2018/0344456, and 2019/0060057, all of which are incorporated herein by reference.

The prosthetic heart valve 10 can also include a valvular structure 18 which is coupled to the frame 12 and configured to regulate the flow of blood through the prosthetic heart valve 10 from the inflow end 14 to the outflow end 16. The prosthetic heart valve 10 can further include a plurality of actuators 80 mounted to and equally spaced around the inner surface of the frame 12. The actuators are configured to apply expansion and compression forces to the frame for radially expanding and compressing the prosthetic valve.

In the illustrated embodiment, the actuators 80 are linear actuators, each of which comprises an inner member, or piston, 90 and an outer member, or cylinder, 92. The inner member 90 is pivotably coupled to a junction of the frame, such as at the first end 14, while the outer member 92 is pivotably coupled to another junction of the frame closer to the second end 16. Moving the inner member 90 proximally relative to the outer member 92 and/or moving the outer member 92 distally relative to the inner member 90 is effective to radially expand the prosthetic valve. Conversely, moving the inner member 90 distally relative to the outer member 92 and/or moving the outer member 92 proximally relative to the inner member 90 is effective to radially compress the prosthetic valve. The actuators 80 can include locking mechanisms that are configured to retain the prosthetic valve in an expanded state inside the patient's body.

In some embodiments, each of the actuators 80 can be configured to form a releasable connection with one or more respective actuators of a delivery apparatus of a transcatheter delivery system. The actuators of the delivery apparatus can transmit forces from a handle of the delivery apparatus to the actuators 80 for expanding or compressing the prosthetic valve. Further details of the actuators, locking mechanisms and delivery apparatuses for actuating the actuators can be found in U.S. Patent Application Publication Nos. 2018/0153689, 2019/0060057 and 2018/0325665, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

In some embodiments, each of the actuators 80 can be used to support a respective commissure 24 (described below). As such, the actuators 80 can include commissure support portions for supporting and attaching commissures 24 of the valvular structure 18 to the frame 12, as described further herein.

The valvular structure 18 can include, for example, a leaflet assembly comprising one or more leaflets 22 (three leaflets 22 in the illustrated embodiment) made of a flexible material. The leaflets 22 of the leaflet assembly can be made from in whole or part, biological material, bio-compatible synthetic materials, or other such materials. Suitable biological material can include, for example, bovine pericardium (or pericardium from other sources). The leaflets 22 can be arranged to form commissures 24, which can be, for example, mounted to commissure support portions of respective actuators 80. Further details regarding transcatheter prosthetic heart valves, including the manner in which the valvular structure can be coupled to the frame 12 of the prosthetic heart valve 10, can be found, for example, in U.S. Pat. Nos. 6,730,118, 7,393,360, 7,510,575, 7,993,394, and 8,652,202, and U.S. Patent Application Publication No. 2018/0325665, all of which are incorporated herein by reference in their entireties.

In some embodiments, as shown in FIG. 1, the commissures 24 can be mounted (e.g., sutured) directly to commissure support portions of the actuators 80 of the frame 12 via commissure attachments 26. As one example, the commissure attachments 26 may include one or more stitches securing the commissures 24 to corresponding actuators 80. In other embodiments, the commissures 24 can be mounted to support struts or posts of the frame that are separate from the actuators 80.

The prosthetic heart valve 10 can also include one or more skirts or sealing members. For example, as shown in FIG. 1, the prosthetic heart valve 10 can include an inner skirt 20 mounted on the inner surface of the frame 12. As shown in FIG. 1, the inner skirt 20 is a circumferential inner skirt that spans an entire circumference of the inner surface of the frame 12. The inner skirt 20 can function as a sealing member to prevent or decrease perivalvular leakage (e.g., when the valve is placed at the implantation site) and as an attachment surface to anchor the leaflets 22 to the frame 12.

The prosthetic heart valve 10 can also include an outer skirt mounted on the outer surface of the frame 12 (not shown in FIG. 1). The outer skirt can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials (e.g., PET) or natural tissue (e.g., pericardial tissue). The inner and outer skirts can be mounted to the frame using sutures, an adhesive, welding, and/or other means for attaching the skirts to the frame.

Since the inner skirt 20 spans the entire circumference of the inner surface of the frame 12, attachment of numerous leaflets (for example, three leaflets) 22 to the inner skirt 20 is time consuming and requires delicate assembly skills to avoid defects that might occur through the process. The skirt 20 is effective to secure the leaflets relative to the frame, though discontinuities 82 can be formed at the attachment region of the leaflet 22 with the inner skirt 20, in the vicinity of corresponding commissure attachments 26 to the frame 12.

Thus, it may be desirable to assemble each leaflet of a leaflet assembly separately, with an individual skirt and leaflet. For example, a leaflet assembly may include a plurality of separately formed leaflet sub-assemblies, each leaflet sub-assembly including a skirt and leaflet secured to one another at a cusp edge portion and commissure (e.g., leaflet) tabs of the leaflet. In some embodiments, the skirt and an additional reinforcing element may form a supporting structure for the leaflet. Each individual leaflet sub-assembly may then be connected to additional leaflet sub-assemblies at adjacently arranged, and individually formed, half commissure portions, thereby forming commissures of the leaflet assembly. The attached leaflet sub-assemblies, forming the leaflet assembly, may then be connected to the frame of the prosthetic heart valve via the formed commissures. Such an assembly process may allow each leaflet sub-assembly to be assembled more quickly and easily, on a relatively flat, two-dimensional platform, prior to being attached to the three-dimensional frame of the prosthetic heart valve.

Figures 2A, 2B:
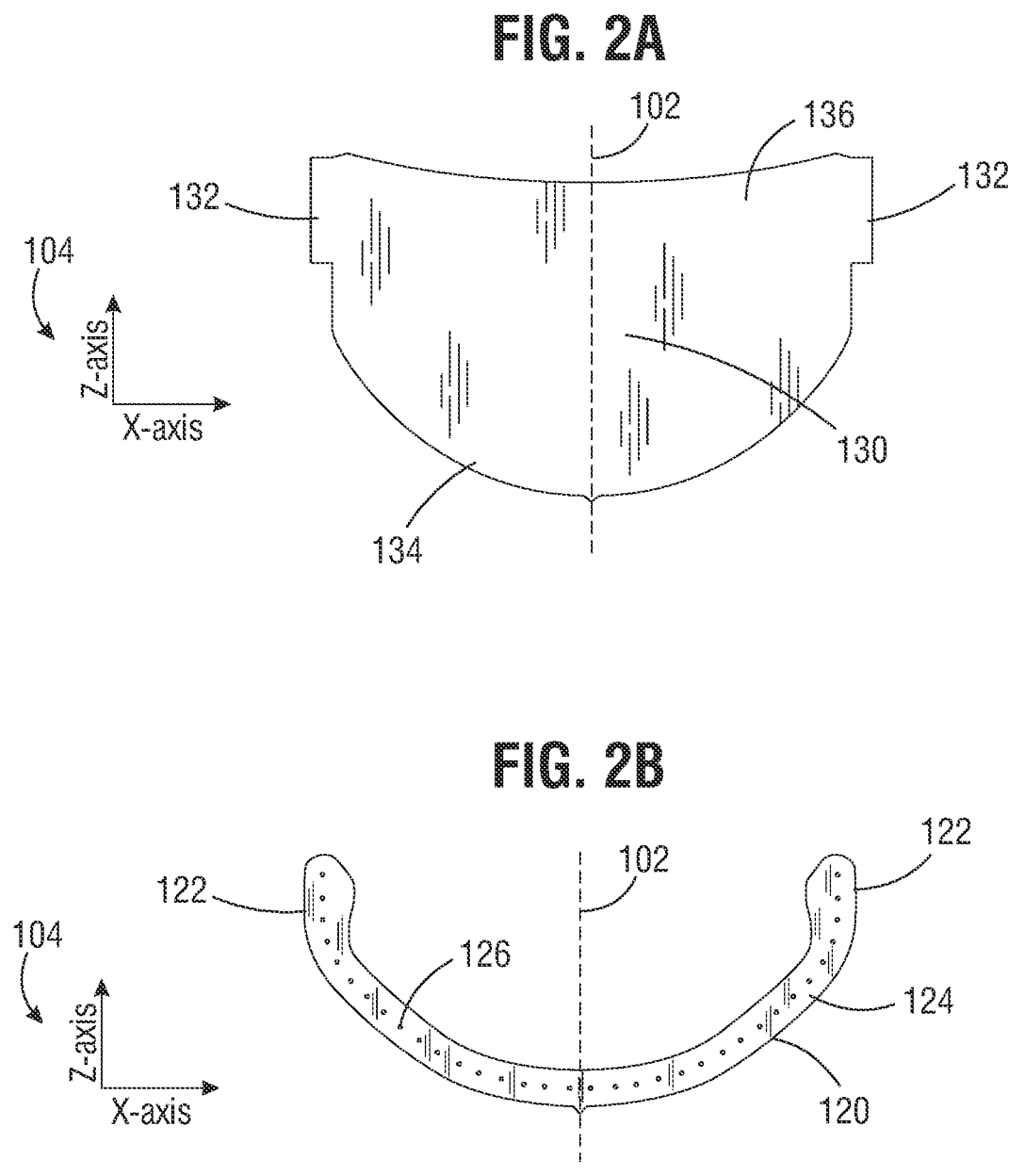
Figure 2C:
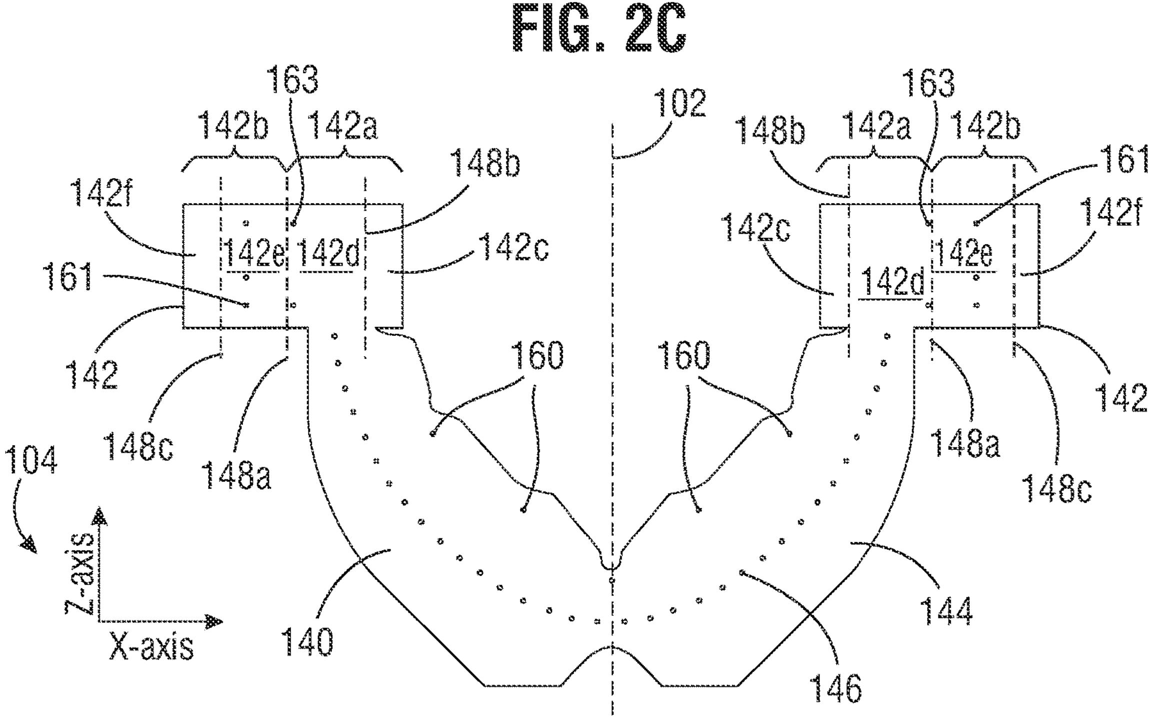

FIGS. 2A-2C show individual components of a leaflet sub-assembly for a prosthetic heart valve. The components of the leaflet sub-assembly can include a leaflet 130 (FIG. 2A), a reinforcing strip 120 (FIG. 2B), and a skirt (e.g., skirt portion) 140 (FIG. 2C). As discussed further below with reference to FIGS. 3-5, the leaflet 130, reinforcing strip 120, and skirt 140 can all be secured to one another to from an individual leaflet sub-assembly 110.

In some embodiments, as shown in FIGS. 6A-7B, multiple leaflet sub-assemblies can be attached to one another. Then, pairs of attached leaflet sub-assemblies can be attached to a commissure support portion (e.g., such as a portion of an actuator or a separate support strut) of the frame of the prosthetic heart valve, as shown by the example embodiments of FIGS. 8-11. Additionally, in some embodiments, the skirt portions of each individual leaflet sub-assembly may be secured to the struts of the frame of the prosthetic heart valve, as shown in FIGS. 11-12.

FIGS. 2A-6B and 8 show reference axes 104 including an x-axis, y-axis, and z-axis. As shown in FIGS. 2A-2C and FIG. 5, the individual components of the leaflet sub-assembly reside in the x-z plane and may be secured to one another is this two-dimensional plane prior to being coupled to another leaflet sub-assembly and/or a frame of the prosthetic heart valve.

As shown in FIG. 2A, the leaflet 130 comprises a main, cusp edge portion 134, two leaflet tabs (also referred to herein as commissure tabs) 132 at opposing ends of the cusp edge portion 134, and an upper edge portion 136. The cusp edge portion 134, leaflet tabs 132, and upper edge portion 136 may be arranged around an outer perimeter of the leaflet 130, with the upper edge portion 136 extending between the two leaflet tabs 132 at an upper edge of the leaflet 130 and the cusp edge portion 134 extending between the two leaflet tabs 132 at a lower edge of the leaflet 130.

As used herein, “upper” and “lower” may be relative to the z-axis which may be arranged parallel with a central longitudinal axis of the prosthetic heart valve when the leaflet assembly is assembled and coupled to a frame of the prosthetic heart valve.

In some embodiments, the cusp edge portion 134 has a curved, scalloped shape (as shown in FIG. 2A). Thus, the cusp edge portion 134 may curve between the two leaflet tabs 132.

FIGS. 2A-2C show a centerline 102 for each of the individual leaflet components, which may also be a centerline of the leaflet sub-assembly. For example, when assembled, the centerlines 102 for each component of the leaflet sub-assembly may overlap. Further, as shown in FIG. 2A, the leaflet tabs 132 may be arranged at opposing ends of the cusp edge portion 134, across the centerline 102 from one another. In some embodiments, the leaflet sub-assembly and/or components of the leaflet sub-assembly may have symmetry (e.g., are reflection symmetric) across the centerline 102.

In some embodiments, as shown in FIG. 2B, the reinforcing strip 120 comprises a middle portion 124 and two end portions 122 arranged at opposing (e.g., opposite) ends of the middle portion 124. The middle portion 124 may be elongated compared to the two end portions 122 and has a curved shape. For example, in some embodiments, the middle portion 124 can have a curved, scalloped shape (as shown in FIG. 2B). In some embodiments, the curved, scalloped shape of the middle portion 124 can match (e.g., track) the curved, scalloped shape of the cusp edge portion 134 of the leaflet 130.

In some embodiments, the reinforcing strip 120 may further include a stitching line 126, which can be, for example, markings (e.g., ink markings) applied to the strip or apertures formed in the strip. For example, as shown in FIG. 2B, the stitching line 126 may be arranged along its center, following the curved shape of the middle portion 124.

In some embodiments, the reinforcing strip 120 can comprise a flexible material. In some embodiments, the reinforcing strip 120 can comprise a fabric material. In other embodiments, the reinforcing strip 120 can comprise a flexible polymeric material.

FIG. 2C shows the skirt 140. The skirt 140 includes a skirt middle portion 144 and two tabs (e.g., skirt tabs) 142 arranged at opposing (e.g., opposite) ends of the skirt middle portion 144. In some embodiments, the skirt 140 further includes a stitching line 146 which may be centered along a length of the skirt middle portion 144 (e.g., extending between the two tabs 142). The stitching line 146 may follow the same contour as the stitching line 126 of the reinforcing strip 120.

According to some embodiments, one or more of the stitching lines 126, 146 comprises an external marking, such as an ink marking, visually indicating suturing or stitching locations for a user assembling the leaflet sub-assembly 110. In some embodiments, one or more of the stitching lines 126, 146 comprises a plurality of apertures or openings, through which a needle carrying sutures (or other yarn, thread, stiches, or the like) can be passed.

The skirt 140 can also include one or more positioning guides 160 arranged along the upper portion of the skirt middle portion 144, and a first column of positioning guides 161 and a second column of positioning guides 163 in each tab 142. The positioning guides 160, 161, and 163 can be markings (e.g., ink markings) on the skirt 140 or apertures formed in the skirt 140. The positioning guides 160 can be used for positioning the middle portion 144 of the skirt relative to struts of the frame when the leaflet assembly is connected to the frame of the prosthetic valve. The positioning guides 163, 161 can be used for positioning the tabs 142 of the skirt 140 relative to the tabs 132 of a corresponding leaflet 130.

In some embodiments, as shown in FIG. 2C, each tab 142 can extend outward from one end of the skirt middle portion 144, in a direction parallel to the centerline 102, and then outward from the portion of the tab 142 that extends outward from the one end of the skirt middle portion 144, in a direction perpendicular to and away from the centerline 102.

Figure 3:
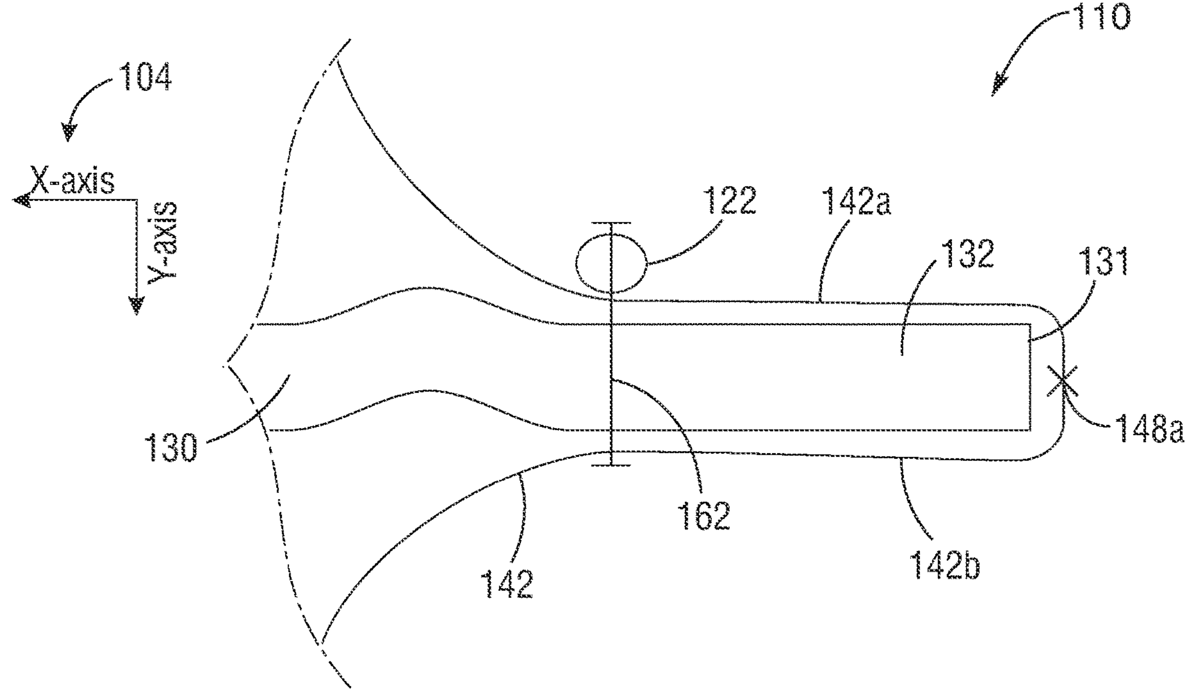
FIG. 3 is a schematic of a first stage of assembling the leaflet sub-assembly, including securing a tab of the skirt to a leaflet tab of the leaflet.
Figure 4:
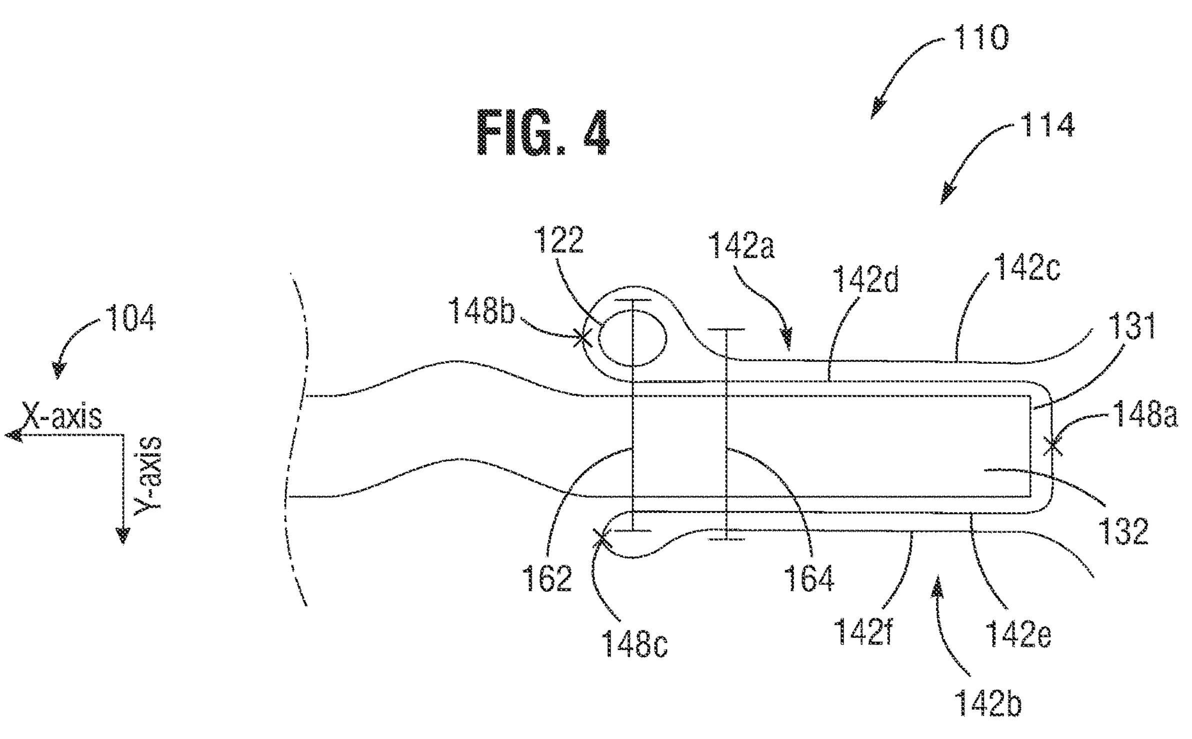
FIG. 4 is a schematic of a second stage of assembling the leaflet sub-assembly, including securing each of folded layers of the tab of the skirt, the leaflet tab of the leaflet, and the reinforcing strip to one another to form a half commissure portion of the leaflet sub-assembly.
Figure 5:
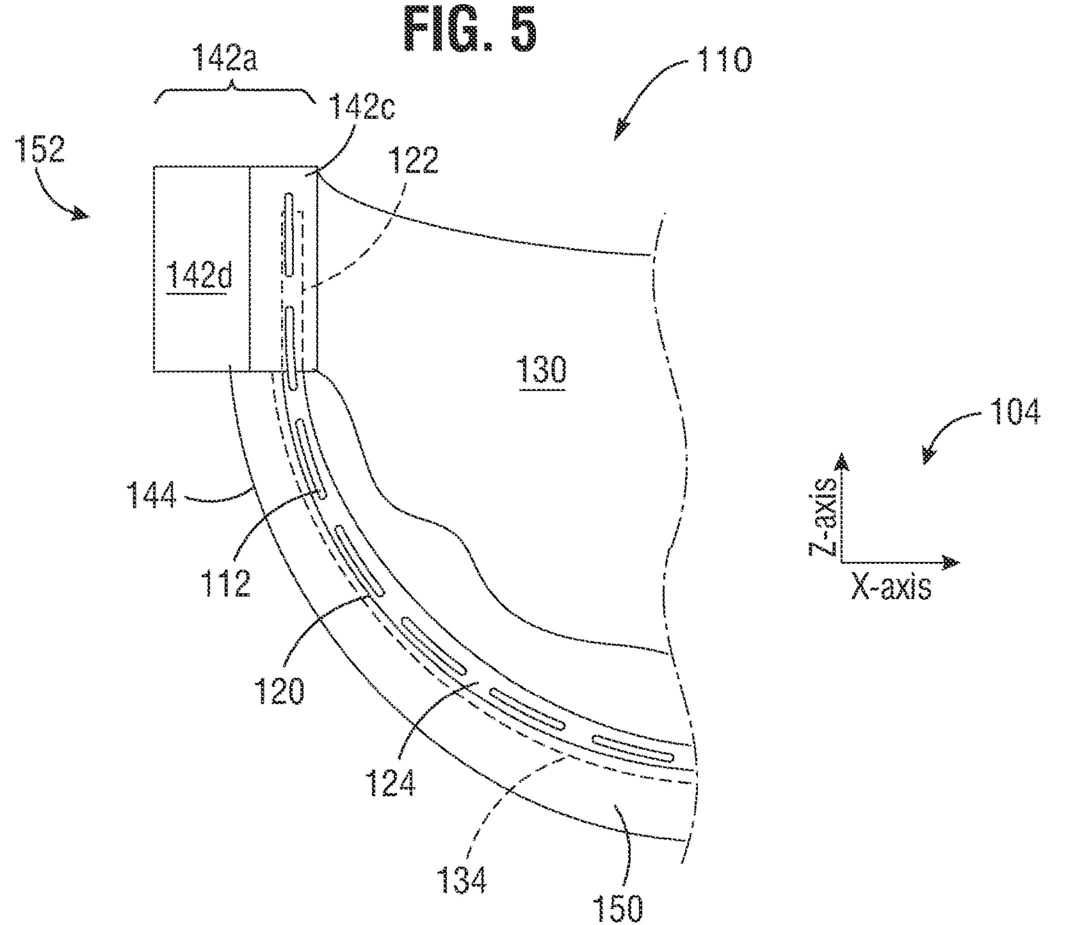
FIG. 5 is a schematic of a third stage of assembling the leaflet sub-assembly, including securing middle portions of each of the leaflet, skirt, and reinforcing strip to one another.

Stages of assembling the leaflet 130, reinforcing strip 120, and skirt 140 into a leaflet sub-assembly 110 are shown in FIGS. 3-8. To assemble the leaflet sub-assembly 110, the skirt 140 can be placed over or against one side of the leaflet 130 (e.g., placed on top of the face of the leaflet 130 shown in FIG. 2A, which is the inner surface of the leaflet once placed inside of the frame). For example, as shown in FIG. 5, the skirt 140 can be placed over (e.g., against) the leaflet 130 such that the skirt middle portion 144 aligns with the cusp edge portion 134 of the leaflet 130 and each tab 142 of the skirt 140 is placed over (e.g., overlaps) a corresponding one of the two leaflet tabs 132 of the leaflet 130. In some embodiments, the skirt 140 may be placed over the leaflet 130 such that the stitching line 146 runs along and/or is arranged adjacent to the curve of the cusp edge portion 134 of the leaflet 130.

Each tab 142 of the skirt 140 can then be folded around a corresponding leaflet tab 132 on the leaflet 130 and secured to the other components of the leaflet sub-assembly 110 via one or more fasteners (e.g., sutures or stitches) to form a half commissure portion for connecting to a half commissure portion of an adjacent leaflet sub-assembly, as described further below. It should be noted that though the forming of these half commissure portions may be described below, with reference to the figures, for one side/end of the leaflet sub-assembly (e.g., for one leaflet tab 132 and one corresponding tab 142 of the skirt 140), the assembly of the half commissure portions may be performed the same for both ends (e.g., on either side of the centerline 102) of the leaflet sub-assembly 110.

Further, while the leaflet sub-assembly is described herein as including the reinforcing strip, in alternate embodiments, the leaflet sub-assembly may not include the reinforcing strip.

As shown in FIG. 2C and FIG. 3, the tab 142 of the skirt 140 can be folded along a first fold line 148*a*, forming two flaps: a first flap 142*a* and a second flap 142*b*. For example, as shown in FIG. 3, the tab 142 is wrapped around the outer edge 131 of the leaflet tab 132 so that the first flap 142*a* covers one side (e.g., first side) of the leaflet tab 132 and the second flap 142*b* covers the other side (e.g., opposite, second side) of the leaflet tab 132. In this way, the tab 142 of the skirt 140 sandwiches the leaflet tab 132.

The reinforcing strip 120 can then be placed on top of (e.g., against) the skirt 140 so that the contour of its middle portion 124 is aligned with the contour of the cusp edge portion 134 of the leaflet 130 and the skirt middle portion 144 of the skirt 140. This may result, for example, in the alignment of the stitching line 126 of the reinforcing strip 120 with the stitching line 146 of the skirt 140. Further, each end portion 122 of the reinforcing strip may be positioned over (e.g., to overlap or overlay) a corresponding first flap 142*a*. Thus, the skirt 140 can be disposed between the reinforcing strip 120 and the leaflet 130 such that a first face or surface of the skirt 140 is positioned or disposed against the leaflet 130 and an opposite, second face or surface of the skirt 140 is positioned or disposed against the reinforcing strip 120.

For example, as shown in FIG. 3 and FIG. 5, an end portion 122 of the reinforcing strip 120 is laid on top of a corresponding first flap 142*a*. The corresponding end portion 122, tab 142, and leaflet tab 132, at a same end or side of the leaflet sub-assembly 110, can then be secured to each other via a fastener. In some embodiments, as shown in FIG. 3, the fastener may be one or more first stitches (e.g., in-and-out stitches formed with a suture) 162 that extend through each of the end portion 122, the first flap 142*a*, the leaflet tab 132, and the second flap 142*b*.

As shown in FIG. 4, an end portion (e.g., free end portion) of the first flap 142*a* can then be folded over the end portion 122 of the reinforcing strip 120 along second fold line 148*b* (see FIG. 2C) to fold back over itself to form an outer first flap portion 142*c* and an inner first flap portion 142*d*. As a result, as shown in FIG. 4, the first flap 142*a* is arranged in two overlapping layers over a first side of the leaflet tab 132. As used herein, the "inner" flap portion is arranged closer to the leaflet tab 132 than the "outer" flap portion and the "outer" flap portion may have an outer, exposed surface.

Similarly, an end portion (e.g., free end portion) of the second flap 142*b* can be folded back over on itself, along third fold line 148*c* (see FIG. 2C), to form an outer second flap portion 142*f* and an inner second flap portion 142*e*. As a result, as shown in FIG. 4, the second flap 142*b* is arranged in two overlapping layers over a second side of the leaflet tab 132.

After making the series of folds described above, the end portion 122 of the reinforcing strip 120 is positioned between the outer first flap portion 142*c* and the inner second flap portion 142*d*, as shown in FIG. 4. Additionally, ends of the first stitch 162 are contained within (e.g., encased by) the folded tab 142 and covered by the outer first flap portion 142*c* and the outer second flap portion 142*f*.

In some embodiments, all of the outer first flap portion 142*c*, the inner first flap portion 142*d*, the outer second flap portion 142*f*, and the inner second flap portion 142*e* are secured to each other via a fastener. For example, as shown in FIG. 4, the fastener may be one or more second stitches 164 (e.g., in-and-out stitches formed with a suture) that extend through each of the outer first flap portion 142*c*, the inner first flap portion 142*d*, the leaflet tab 132, the inner second flap portion 142*e*, and the outer second flap portion 142*f*.

In some embodiments, as shown in FIG. 4, the second stitch 164 may be arranged adjacent to the first stitch 162 and outside of the first stitch 162 relative to the outer edge 131 of the leaflet tab 132. In other embodiments, the second stitch 164 may be located further away from the first stitch 162 than shown in FIG. 4, such as further toward the outer edge 131 of the leaflet tab 132.

The combination of the secured together leaflet tab 132, all flap portions of the tab 142, and the end portion 122 of the reinforcing strip 120 (as described above with reference to FIGS. 3-4) may be referred to herein as a half commissure portion 114 (as shown in FIG. 4). Each leaflet sub-assembly, such as leaflet sub-assembly 110, includes two formed half commissure portions 114 (e.g., one on either side of centerline 102). As described further below, adjacently arranged half commissure portions of two leaflet sub-assemblies may be secured to one another, to form a commissure (e.g., where two adjacent portions of two leaflet sub-assemblies are connected together), prior to attaching the leaflet sub-assemblies to a frame of the prosthetic heart valve.

As shown in FIG. 5, in some embodiments, the leaflet 130, the skirt 140, and the reinforcing strip 120 can be further secured to each other with an additional fastener, such as stitches (e.g., of one or more sutures) 112. For example, in-and-out stitches 112 can extend through the middle portion 124 of the reinforcing strip 120, the skirt middle portion 144 of the skirt 140, and the cusp edge portion 134 of the leaflet 130, along at least a portion of the length of a curved, outer edge 150 of the leaflet sub-assembly 110. For example, as shown in FIG. 5, the in-and-out stitches 112 can extend through the middle portion 124 of the reinforcing strip 120, the skirt middle portion 144 of the skirt 140, and the cusp edge portion 134 of the leaflet 130, from a first end 152 of the leaflet sub-assembly 110 (e.g., at one of the two tabs 142) to the opposite, second end of the leaflet sub-assembly 110 (e.g., at another one of the two tabs 142, not shown in FIG. 5). The stitches 112 can also extend through the half commissure portions at opposite ends of the leaflet sub-assembly, as shown.

In some embodiments, the in-and-out stitches 112 may follow and extend through and along the stitching line 126 and the stitching line 146.

In some embodiments, the combination of the leaflet 130, the skirt 140, and the reinforcing strip 120 forms the leaflet sub-assembly. Leaflet sub-assemblies can be formed separately, as described above, for each of the leaflets of a prosthetic valve (e.g., each of three leaflets). For example, each leaflet sub-assembly may be formed individually, in a relatively flat plane (e.g., the x-z plane shown in FIG. 5), prior to being attached to a frame of the prosthetic heart valve.

After forming one or more individual leaflet sub-assemblies, such as leaflet sub-assembly 110, pairs of leaflet sub-assemblies, intended to be arranged adjacent to one another within a prosthetic heart valve frame, can then be attached to each other with additional fasteners, prior to attachment to the frame of the prosthetic heart valve.

For example, as shown in FIGS. 6A-6B and FIGS. 7A-7B, adjacent leaflet sub-assemblies (formed in a same manner and including similar components as the leaflet sub-assembly 110) including a first leaflet sub-assembly 110' and a second leaflet sub-assembly 110", can be positioned so that a first half commissure portion 114' of the first leaflet sub-assembly 110' is arranged adjacent to a second half commissure portion 114" of the second leaflet sub-assembly 110".

For example, this positioning may result in the outer second flap portions **142*f* (of first leaflet sub-assembly 110') and 142*f*" (of second leaflet sub-assembly 110") being arranged adjacent to one another. In this configuration, the reinforcing strip 122' of the first leaflet sub-assembly 110' and the reinforcing strip 122" of the second leaflet sub-assembly 110" are arranged apart from one another, on outer edges of the assemblies, so that the reinforcing strips 122' and 122"** are not sandwiched between the adjacently arranged leaflet tabs.

The first leaflet sub-assembly 110' and the second leaflet sub-assembly 110" may then be attached to one another via a fastener, such as stitching (e.g., suture) 166. This fastening may be repeated for each pair of adjacently arranged leaflet sub-assemblies, on either side of the leaflet sub-assemblies (e.g., for each set of half commissure portions).

Figures 6A, 6B:
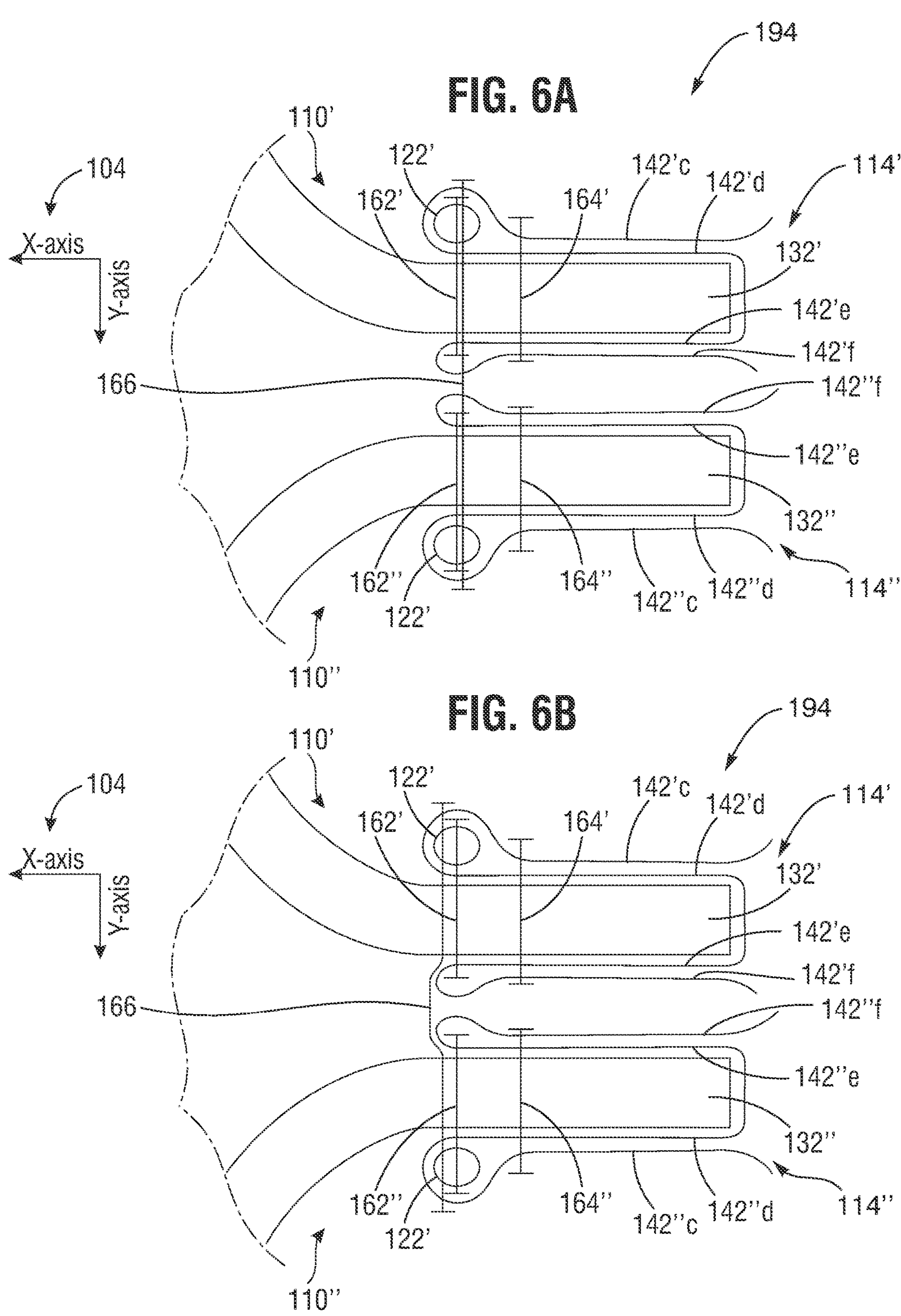
FIGS. 6A-6B are schematics of embodiments of attaching adjacent leaflet sub-assemblies to one another to form a commissure.

As shown in FIGS. 6A-6B, the stitching 166 extends through the tab 142' (through at least some of flap portions 142'*c-f*), end portion 122' of the reinforcing strip 120', and the leaflet tab 132' of the first leaflet sub-assembly 110' and the tab 142" (through at least some of flap portions 142"*c-f*), end portion 122" of the reinforcing strip 120", and the leaflet tab 132" of the adjacent, second leaflet sub-assembly 110".

In some embodiments, the stitching 166 is positioned adjacent to stitching 162' and 162", on a side facing stitching 164' and 164", as depicted in FIG. 6A. In other embodiments, as depicted in FIG. 6B, the stitching 166 is positioned adjacent to stitching 162' and 162", on an opposite side of the stitching 162' and 162" from the stitching 164' and 164".

In some embodiments, as shown in FIG. 6A, the stitching 166 extends through the outer first flap portion **142*c*', the reinforcing strip end portion 122', the inner first flap portion 142*d*', the leaflet tab 132', the inner second flap portion 142*e*', the outer second flap portion 142*f*, the outer second flap portion 142*f*', the inner second flap portion 142*e*", the leaflet tab 132", the inner first flap portion 142*d*", the reinforcing strip end portion 122", and the outer first flap portion 142*c*"**.

According to other embodiments, as shown in FIG. 6B, the stitching 166 extends through the outer first flap portion **142*c*', the reinforcing strip end portion 122', the inner first flap portion 142*d*', the leaflet tab 132', the leaflet tab 132", the inner first flap portion 142*d*", the reinforcing strip end portion 122", and the outer first flap portion 142*c*", without extending through any of the inner second flap portion 142*e*', the outer second flap portion 142*f*, the outer second flap portion 142*f*', and the inner second flap portion 142*e*"**.

The secured together (e.g., attached) first half commissure portion 114' and second half commissure portion 114" may be referred to herein as a commissure 194 of the two adjacent leaflet sub-assemblies.

Figure 7A:
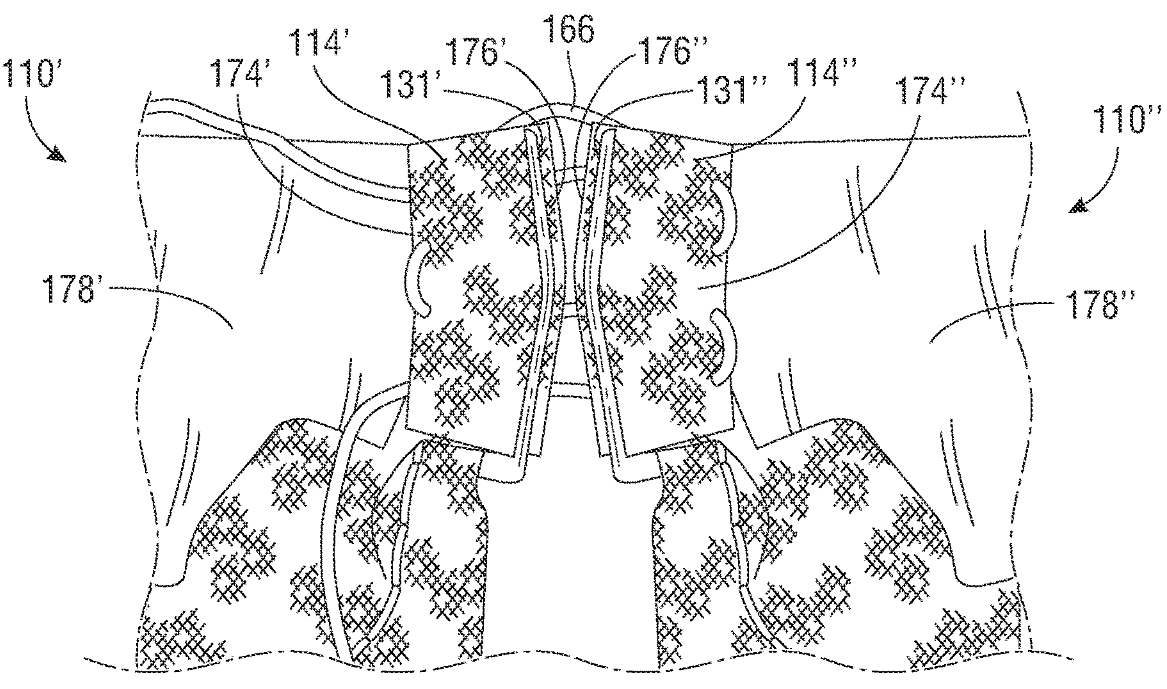
FIGS. 7A-7B are plan views of a portion of a first leaflet sub-assembly and a portion of a second leaflet sub-assembly positioned side-by-side in a relatively flat, two-dimensional plane so that a first half commissure portion of the first leaflet sub-assembly can be secured to a second half commissure portion of the second leaflet sub-assembly.
Figure 7B:
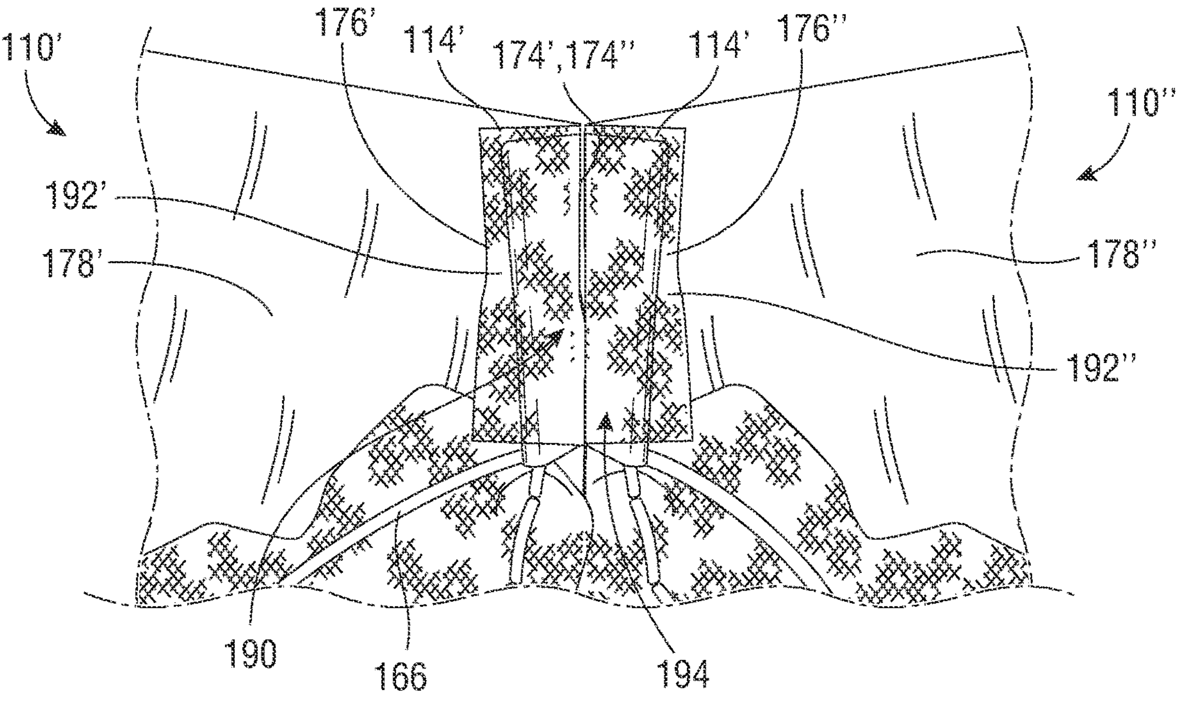

FIGS. 7A-7B show views of a portion of the first leaflet sub-assembly 110' and a portion of the second leaflet sub-assembly 110" positioned side-by-side one another in a relatively flat, two-dimensional plane (e.g., the x-z plane that each sub-assembly was individually assembled in in FIGS. 2A-5) so that a first half commissure portion 114' of the first leaflet sub-assembly 110' is arranged directly adjacent to a second half commissure portion 114" of the second leaflet sub-assembly 110".

As shown in FIG. 7A, prior to fastening the two half commissure portions of the first and second leaflet sub-assemblies to one another (e.g., via tightening the stitching 166), outer edges 176' and 176" of the half commissure portions, including the outer edge of 131' of the leaflet tab 132' and the outer edge 131" of the leaflet tab 132" are facing one another. Then, as shown in FIG. 7B, upon tightening the stitching 166, at bases 174' and 174" of the two half commissure portions 114' and 114", the outer edges 176' and 176" of the half commissure portions are facing up (e.g., out of the page in FIG. 7B).

As shown in FIG. 7A, the base 174', 174" of each half commissure portion 114', 114" is arranged opposite the respective outer edge 176', 176" of the half commissure portion, proximate to a cusp 178', 178" of a corresponding leaflet.

As shown in FIG. 7B, securing the two half commissure portions 114' and 114" together at their bases 174' and 174" creates a gap 190 between an inner face 192' of the first half commissure portion 114' and an inner face 192" of the second half commissure portion 114". The gap 190 can be adapted to receive a commissure support portion (e.g., support strut) of a frame of a prosthetic heart valve, as described further below. The attached half commissure portions 114' and 114" form the commissure 194 of the two adjacent leaflet sub-assemblies.

Figure 8:
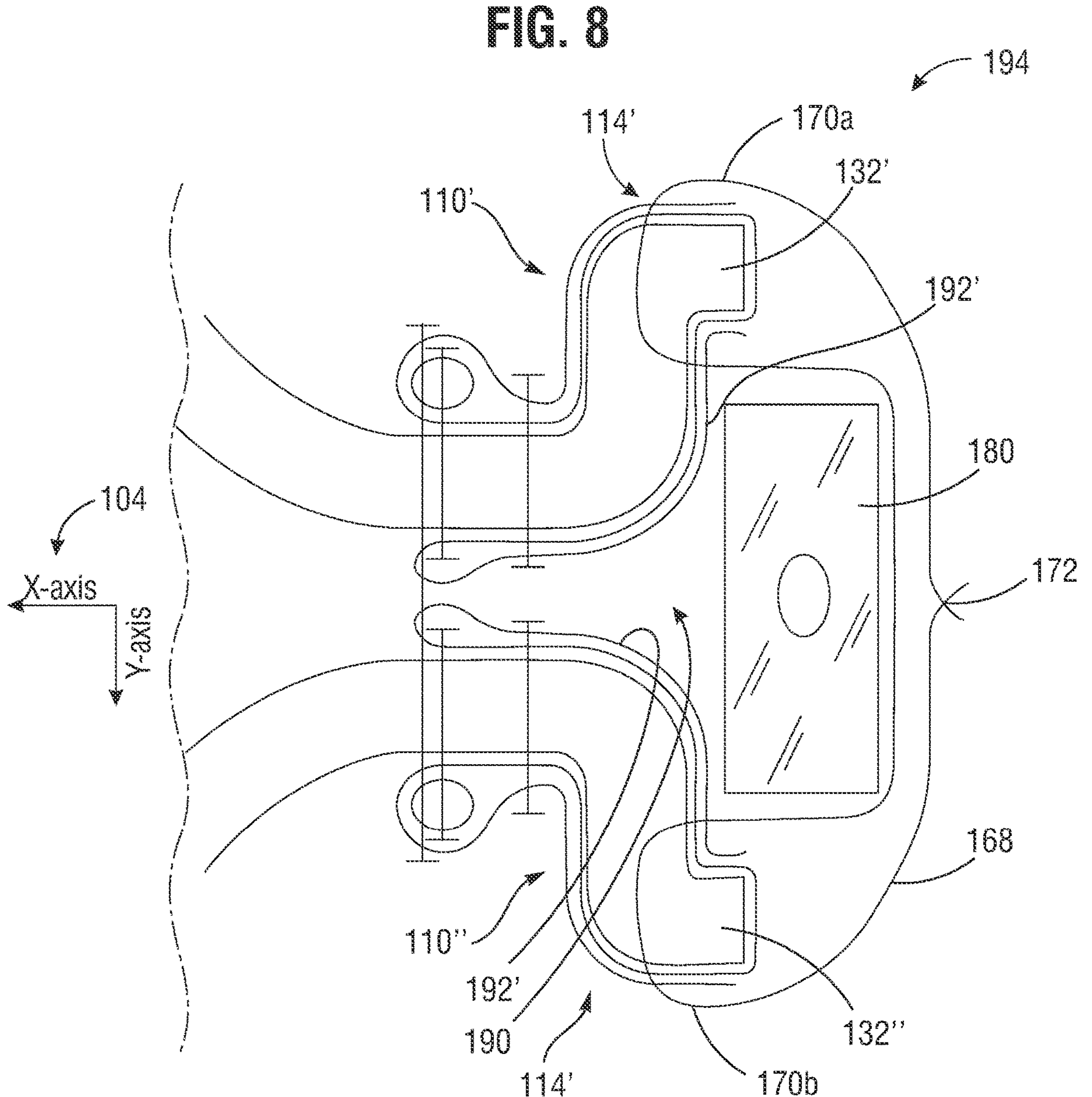
FIG. 8 is a schematic showing an embodiment of attaching a commissure of a pair of attached leaflet sub-assemblies to a commissure support portion of a frame of a prosthetic heart valve.

For example, as shown in FIG. 8, the pair of attached leaflet sub-assemblies, including the first leaflet sub-assembly 110' and the second leaflet sub-assembly 110", can then be attached to a commissure support portion (e.g., support strut) 180 of the frame of the prosthetic heart valve. The commissure support portion 180 can be a portion of an actuator 80 (e.g., an upper portion of outer member 92), as shown in FIG. 1, or a separate support strut or post of the frame. In some embodiments, as shown in FIG. 8, the commissure 194, formed by the attached first half commissure portion 114' and the second half commissure portion 114", can be attached to the commissure support portion 180 using a fastening element, such as a suture 168.

As shown in FIG. 8, each half commissure portion 114', 114" can be at least partially wrapped around the commissure support portion 180. The suture 168 can be stitched through end portions of each half commissure portion of each leaflet sub-assembly 110' and 110" using two stitches **170*a* and 170*b*. The opposing ends of the two stitches 170*a* and 170*b* can be tied together on the outside (e.g., outer surface) of the commissure support portion 180 and frame, at tie 172**, for example. In other embodiments, a separate suture can be tied to each half commissure portion and then tied to one another.

Turning now to FIGS. 9-12, an embodiment of a prosthetic heart valve 200 and a method for attaching a pair of leaflet sub-assemblies, attached together at a commissure 214, to a frame 202 of the prosthetic heart valve 200 is shown. For example, a first leaflet sub-assembly 210 and a second leaflet sub-assembly 212 shown in FIGS. 9-12 may be similar to the leaflet sub-assemblies 110, 110', and/or 110" described above with reference to FIGS. 2A-8, and thus, may include the same or similar components. Further, the first leaflet sub-assembly 210 and the second leaflet sub-assembly 212 may be secured to one another, forming the commissure 214, in a same or similar manner as described above with reference to FIGS. 2A-7B.

FIGS. 9-12 show an embodiment of a prosthetic heart valve 200 having a frame 202. Similarly to as described above with reference to FIG. 1, the frame 202 can include a plurality of interconnected struts 204 and a plurality of actuators 205, 206, 207 mounted to and equally spaced around the inner surface of the frame 202. In the illustrated embodiment, the actuators are used to support the commissures and therefore components of the actuators are referred to as commissure support portions in the following description, although it should be understood that the frame can include commissure support portions that are separate from the actuators.

Unlike the prosthetic heart valve 10 of FIG. 1, the prosthetic heart valve 200 does not include a single inner skirt extending around an entire circumference of the frame. Instead, the prosthetic heart valve 200 includes a plurality of leaflet sub-assemblies (e.g., three), including the first leaflet sub-assembly 210 and the second leaflet sub-assembly 212, which each include a leaflet and discrete skirt portion (e.g., leaflet 130 shown in FIG. 2A and skirt 140 shown in FIG. 2C) that are preassembled prior to being attached to the frame 202, as described above with reference to FIGS. 2A-7B.

For example, looking specifically at one leaflet sub-assembly, the first leaflet sub-assembly 210 includes an individual leaflet 208 and individual skirt 218. The first leaflet sub-assembly 210 has a first half commissure portion 220 secured to a first half commissure portion 222 of the second leaflet sub-assembly 212 to form the commissure 214. Further, the first leaflet sub-assembly 210 includes a second half commissure portion 224, arranged on an opposite side of the first leaflet sub-assembly 210 from the first half commissure portion 220 (see FIG. 12). The second half commissure portion 224 of the first leaflet sub-assembly 210 is attached to a first half commissure portion of a third leaflet sub-assembly to form a second commissure 226 (see FIG. 12). A second half commissure portion of the third leaflet sub-assembly can be attached to a second half commissure portion of the second leaflet sub-assembly 212 to form a third commissure of the prosthetic heart valve 200 (not seen in the views of FIGS. 9-12).

As shown in FIGS. 11-12, the commissure 214 of the first leaflet sub-assembly 210 and the second leaflet sub-assembly 212 is attached to a first support strut 206 of the frame 202 via a fastening element (e.g., sutures or stitches) 216. The fastening element 216 can comprise a plurality of stitches, in some embodiments. The fastening element 216 may be similar to the stitches **170*a* and 170*b* shown in FIG. 8. The support strut 206 can be the outer member of an actuator (e.g., similar to outer member 92 of actuator 80**).

Figure 9:
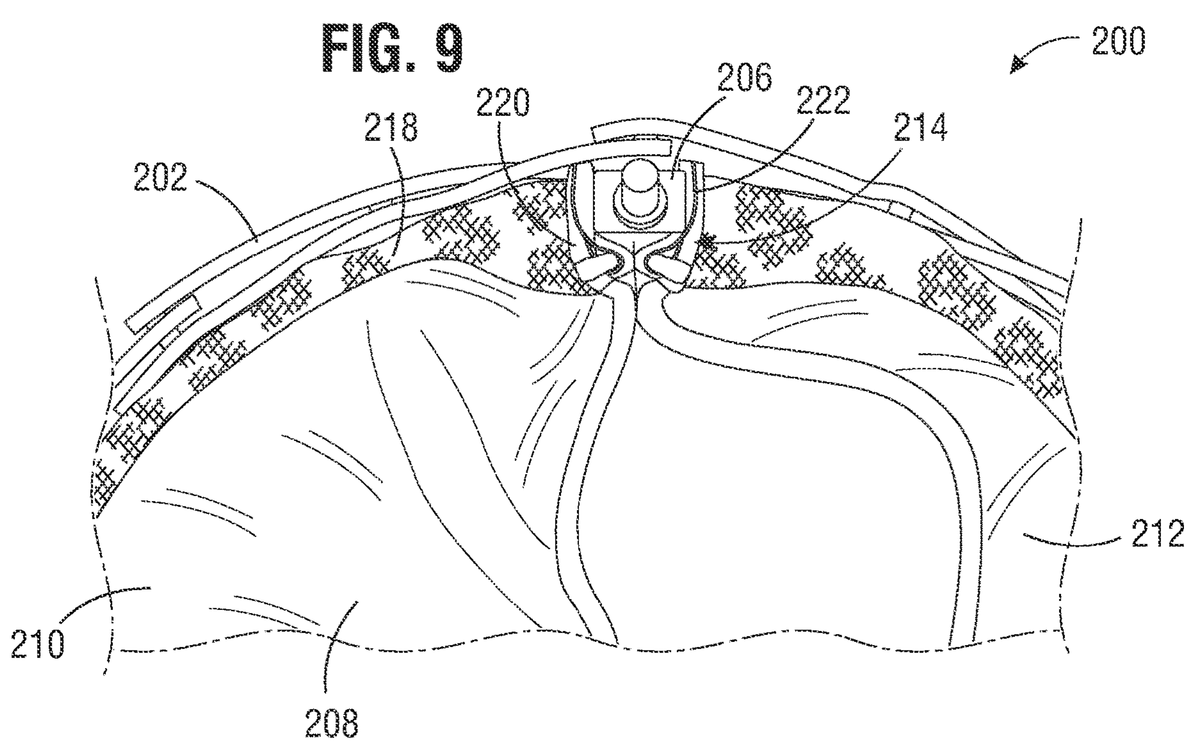
FIG. 9 is a top view of an exemplary embodiment of an attachment of a commissure of a pair of leaflet sub-assemblies to a commissure support portion of a frame of a prosthetic heart valve.
Figure 10:
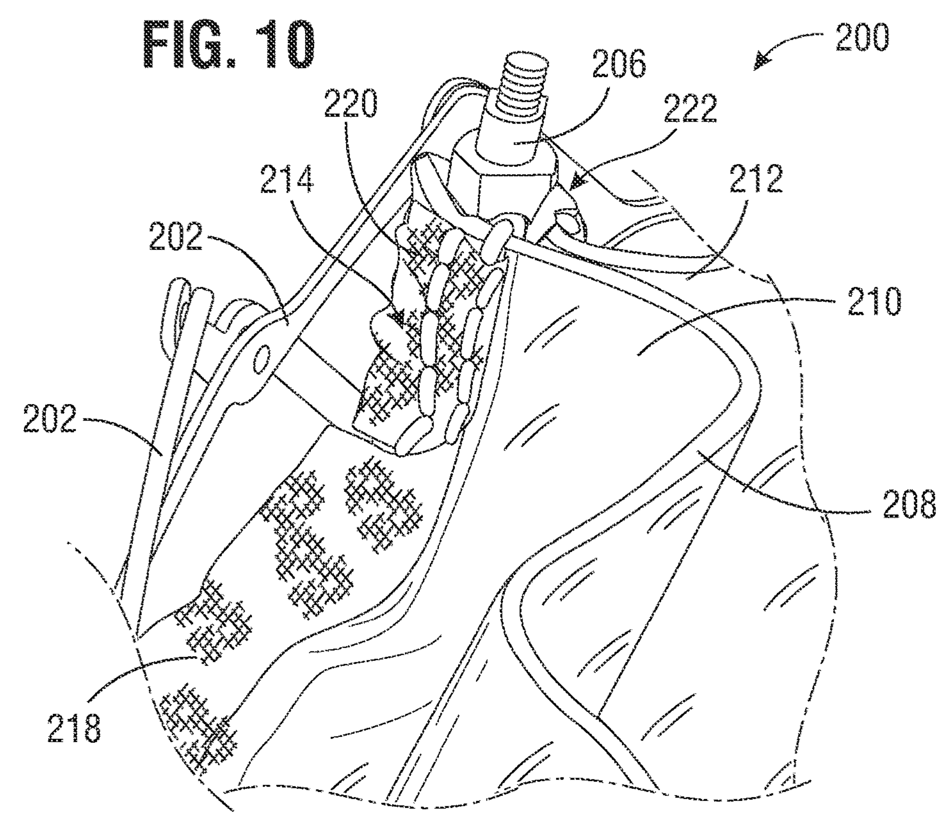
FIG. 10 is a perspective view of the exemplary embodiment of FIG. 9.
Figures 11, 12:
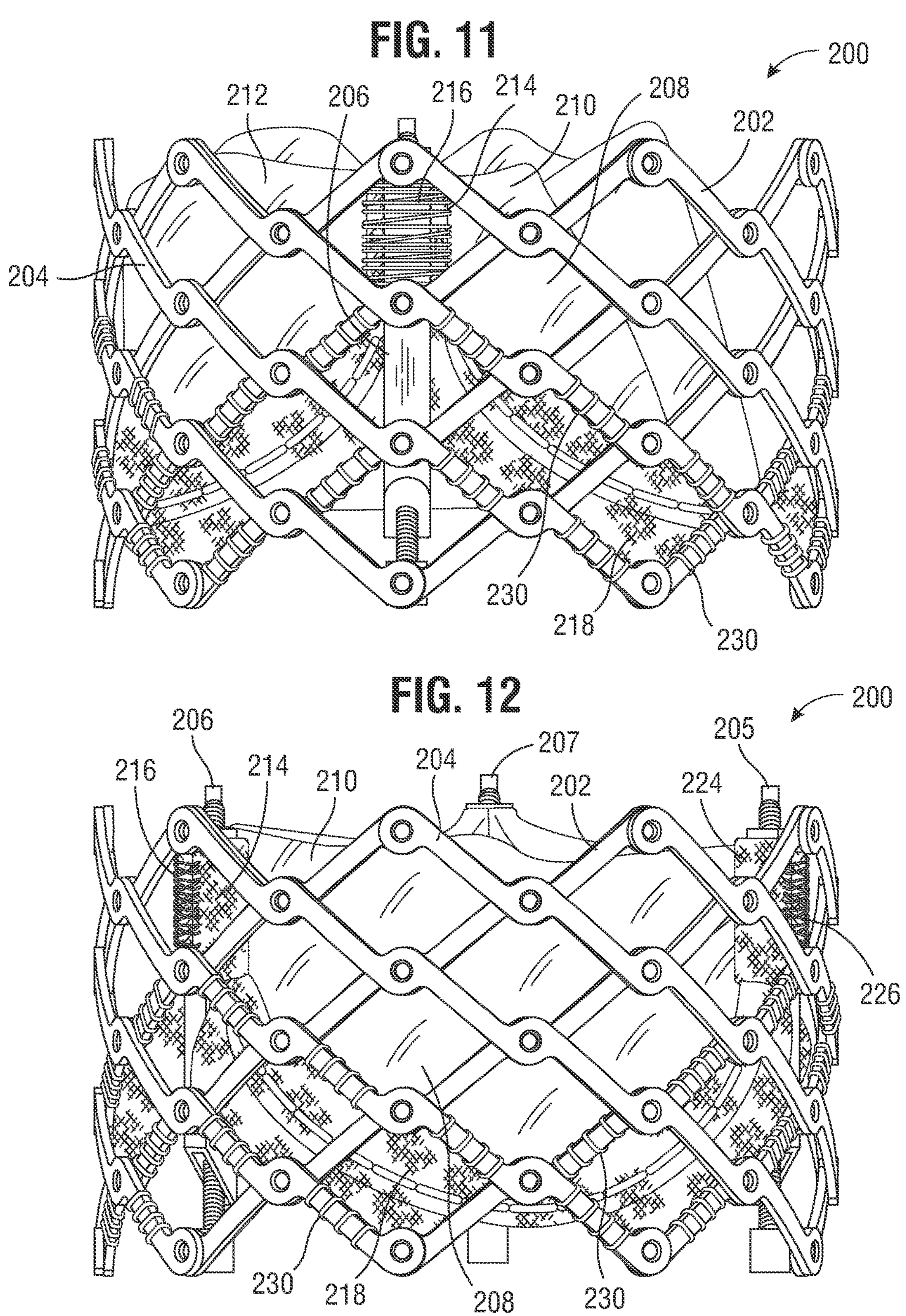
FIG. 11 is a first side view of the exemplary embodiment of FIG. 9 that also shows an embodiment of an attachment of the individual skirts of the pair of leaflet sub-assemblies to the frame of the prosthetic heart valve.
FIG. 12 is a second side view of the exemplary embodiment of FIG. 9 that also shows the embodiment of the attachment of the individual skirts of the pair of leaflet sub-assemblies to the frame of the prosthetic heart valve.

For example, as shown in FIGS. 9 and 10, outer ends of the commissure 214 are wrapped around the first support strut 206, toward a front surface of the first support strut 206. The fastening element 216, including a series of stitches, are attached to either end of the commissure 214 and then extend across and around the front (e.g., outer) surface of the first support strut 206 (see FIGS. 11 and 12).

In some embodiments, as shown in FIGS. 11 and 12, the skirt of each leaflet sub-assembly (e.g., skirt 218 of first leaflet sub-assembly 210) may be secured (e.g., attached) to the struts 204 of the frame 202 via a fastener 230. In some embodiments, the fastener 230 may include one or more sutures or stitches extending along the upper and lower edges of the skirt middle portion of the skirt 218. The stitches 230 can extend around adjacent struts 204 that extend along the upper and lower edges of the skirt.

Thus, instead of attaching individual leaflets to a single inner skirt of the frame of the prosthetic heart valve (as shown in FIG. 1), the skirt of each individual leaflet sub-assembly may be attached directly to the struts 204 of the frame 202 and each commissure (e.g., three total in the embodiment of FIGS. 9-12) may be attached to a respective support strut of the frame 202. Since the leaflet and skirt of each leaflet sub-assembly and each commissure are already secured together, prior to attachment to the frame 202, an overall assembly of the leaflet assembly (comprising the attached leaflet sub-assemblies) and attachment of the leaflet assembly to the frame 202 may be simplified and take less time than traditional attachment methods (as described above with reference to FIG. 1).

In this way, leaflet sub-assemblies, each including a skirt and a leaflet, can be preassembled prior to attachment to a frame of a prosthetic heart valve. For example, as described above, assemblage of each leaflet sub-assembly can be performed in a simpler manner, on a relatively flat surface, instead of a complex leaflet attachment to a three-dimensional structure of a standard skirt disposed along the inner surface of the frame of the prosthetic heart valve. Further, by pre-assembling the leaflet sub-assemblies, individually, any identified defects in one or more leaflet sub-assemblies can be addressed prior to forming a complete valvular structure (e.g., leaflet assembly including multiple leaflets attached to a standard skirt of a prosthetic heart valve). Further still, leaflet sub-assemblies can be attached to the frame of the prosthetic heart valve in a simpler and faster manner, as compared to attaching each leaflet to a three-dimensional skirt already attached to the frame of the prosthetic heart valve.

GENERAL CONSIDERATIONS

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used herein, with reference to the prosthetic heart valve and the transcatheter delivery system, "proximal" refers to a position, direction, or portion of a component that is closer to the user and a handle of the delivery system that is outside the patient, while "distal" refers to a position, direction, or portion of a component that is further away from the user and the handle and closer to the implantation site. The terms "longitudinal" and "axial" refer to an axis extending in the proximal and distal directions, unless otherwise expressly defined.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and or.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of assembling a prosthetic heart valve including a leaflet assembly, comprising:

forming a plurality of leaflet sub-assemblies, each leaflet sub-assembly including a leaflet and a skirt, wherein each leaflet sub-assembly is formed by:

placing the skirt on one side of the leaflet such that the skirt extends along a curved cusp edge portion of the leaflet and two commissure tabs of the leaflet, wherein the skirt lies in an x-z plane defined by an x-axis and a z-axis, the x-axis extending from side to side of the skirt and the z-axis extending from an inflow end to an outflow end of the skirt, wherein the skirt comprises a middle portion extending between two end portions, wherein each of the two end portions of the skirt comprises a tab comprising a first flap and a second flap, the first flap connected to and extending upwardly in a direction of the z-axis from an upper end of the middle portion of the skirt, and the second flap extending laterally from the first flap in a direction of the x-axis such that the second flap is offset from the middle portion in the direction of the x-axis;

folding the two end portions of the skirt around corresponding commissures tabs of the leaflet, wherein folding the two end portions of the skirt around corresponding commissure tabs of the leaflet includes, for each end portion and corresponding commissure tab, folding the tab around the corresponding commissure tab such that the first flap of the tab covers a first side of the commissure tab and the second flap of the tab covers a second side of the commissure tab;

stitching each folded end portion to the corresponding commissure tab of the two commissure tabs to form a respective half commissure portion of the leaflet sub-assembly; and stitching the skirt to the cusp edge portion of the leaflet;

forming the leaflet assembly by pairing each half commissure portion of each leaflet sub-assembly with a half commissure portion of another leaflet sub-assembly of the plurality of leaflet sub-assemblies to form a plurality of pairs of adjacent half commissure portions, and for each pair, stitching the adjacent half commissure portions to each other to form a commissure of the leaflet assembly; and securing the leaflet assembly to a frame of the prosthetic heart valve via fastening each commissure to a commissure support portion of the frame.

2. The method of claim 1, further comprising, further securing the leaflet assembly to the frame of the prosthetic heart valve via fastening the skirt of each leaflet sub-assembly to struts of the frame, and wherein fastening the skirt of each leaflet sub-assembly to struts of the frame includes fastening the middle portion of the skirt of each leaflet sub-assembly to a plurality of interconnected struts of the frame that are arranged in a lattice-type pattern.

3. The method of claim 1, wherein fastening each commissure to a commissure support portion of the frame includes wrapping end portions of each commissure around a respective commissure support portion and stitching through the end portions of the commissure via one or more sutures and tying the one or more sutures together on an outer surface of the commissure support portion of the frame.

4. The method of claim 1, further comprising, for each end portion and corresponding commissure tab, folding the first flap over itself to form two overlapping layers of the first flap on the first side of the commissure tab and folding the second flap over itself to form two overlapping layers of the second flap on the second side of the commissure.

5. The method of claim 1, wherein the middle portion of the skirt of each leaflet sub-assembly is disposed on only the one side of a corresponding leaflet.

6. A method of assembling a prosthetic heart valve including a leaflet assembly, comprising:

forming a plurality of leaflet sub-assemblies, each leaflet sub-assembly including a leaflet and a skirt, wherein each leaflet sub-assembly is formed by placing the skirt on one side of the leaflet such that the skirt extends along a curved cusp edge portion of the leaflet and two commissure tabs of the leaflet, folding two end portions of the skirt around corresponding commissures tabs of the leaflet, stitching each folded end portion to a corresponding commissure tab of the two commissure tabs to form a respective half commissure portion of the leaflet sub-assembly, and stitching the skirt to the cusp edge portion of the leaflet;

forming the leaflet assembly by pairing each half commissure portion of each leaflet sub-assembly with a half commissure portion of another leaflet sub-assembly of the plurality of leaflet sub-assemblies to form a plurality of pairs of adjacent half commissure portions, and for each pair, stitching the adjacent half commissure portions to each other to form a commissure of the leaflet assembly; and securing the leaflet assembly to a frame of the prosthetic heart valve via fastening each commissure to a commissure support portion of the frame, wherein each of the two end portions of the skirt includes a tab and wherein folding the two end portions of the skirt around corresponding commissure tabs of the leaflet includes, for each end portion and corresponding commissure tab, folding the tab around the corresponding commissure tab to form a first flap covering a first side of the commissure tab and a second flap covering a second side of the commissure tab, and wherein each leaflet sub-assembly further includes a reinforcing strip and further comprising placing the reinforcing strip on a side of the skirt arranged opposite a side of the skirt placed on the leaflet such that the reinforcing strip extends along a curved portion of the skirt and each of two end portions of the reinforcing strip overlay a corresponding first flap of the skirt and stitching each folded end portion of the skirt to the corresponding commissure tab and a corresponding end portion of the two end portions of the reinforcing strip via a first stitch.

7. The method of claim 6, wherein folding the two end portions of the skirt around corresponding commissure tabs of the leaflet further includes, for each end portion of the skirt and corresponding commissure tab, folding a free end portion of the first flap back over itself to cover the corresponding end portion of the reinforcing strip and form two overlapping layers over the first side of the commissure tab and folding a free end portion of the second flap back over itself to form two overlapping layers over the second side of the commissure tab, and further comprising stitching the two overlapping layers over the first side of the commissure tab, the commissure tab, and the two overlapping layers over the second side of the commissure tab to one another via a second stitch.

8. The method of claim 7, wherein, for each pair of adjacent half commissure portions, stitching the adjacent half commissure portions to each other to form a commissure of the leaflet assembly includes stitching the adjacent half commissure portions to each other via a third stitch arranged adjacent to the first stitch, the third stitch extending through the corresponding end portion of the reinforcing strip of each leaflet sub-assembly.

9. The method of claim 8, wherein stitching the adjacent half commissure portions to each other via the third stitch includes extending the third stitch through the two overlapping layers over the first side of the commissure tab, the commissure tab, and the two overlapping layers over the second side of the commissure tab, for each half commissure portion of the pair of adjacent half commissure portions, and wherein the third stitch is arranged adjacent to the first stitch on a side of the first stitch that faces the second stitch.

10. The method of claim 8, wherein stitching the adjacent half commissure portions to each other via the third stitch includes extending the third stitch through the two overlapping layers over the first side of the commissure tab and the commissure tab, and not the two overlapping layers over the second side of the commissure tab, for each half commissure portion of the pair of adjacent half commissure portions, and wherein the third stitch is arranged adjacent to the first stitch on a side of the first stitch that is arranged opposite to a side of the first stitch that faces the second stitch.

* * * * *